United States Patent
Liu et al.

(10) Patent No.: US 12,186,757 B2
(45) Date of Patent: Jan. 7, 2025

(54) DEVICES AND METHODS FOR MONITORING AND QUANTIFYING NUCLEIC ACID AMPLIFICATION

(71) Applicant: THE TRUSTEES OF THE UNIVERSITY OF PENNSYLVANIA, Philadelphia, PA (US)

(72) Inventors: Changchun Liu, Bala Cynwyd, PA (US); Haim H. Bau, Swarthmore, PA (US)

(73) Assignee: THE TRUSTEES OF THE UNIVERSITY OF PENNSYLVANIA, Philadelphia, PA (US)

(*) Notice: Subject to any disclaimer, the term of this patent is extended or adjusted under 35 U.S.C. 154(b) by 297 days.

(21) Appl. No.: 15/323,193

(22) PCT Filed: Jul. 1, 2015

(86) PCT No.: PCT/US2015/038739
§ 371 (c)(1),
(2) Date: Dec. 30, 2016

(87) PCT Pub. No.: WO2016/004155
PCT Pub. Date: Jan. 7, 2016

(65) Prior Publication Data
US 2017/0128947 A1   May 11, 2017

Related U.S. Application Data

(60) Provisional application No. 62/020,484, filed on Jul. 3, 2014, provisional application No. 62/020,135, filed on Jul. 2, 2014.

(51) Int. Cl.
*C12Q 1/686* (2018.01)
*B01L 3/00* (2006.01)
*B01L 7/00* (2006.01)

(52) U.S. Cl.
CPC ............ *B01L 7/54* (2013.01); *B01L 3/50273* (2013.01); *C12Q 1/686* (2013.01);
(Continued)

(58) Field of Classification Search
CPC ..... B01L 2300/0816; B01L 2400/0472; B01L 2400/0677; C12Q 1/686; C12Q 2565/631; C12Q 1/68
See application file for complete search history.

(56) References Cited

U.S. PATENT DOCUMENTS 5,984,257 A   11/1999   Baek et al.
9,233,368 B2   1/2016   Bau et al.
(Continued)

FOREIGN PATENT DOCUMENTS

WO   WO-2013103360 A1 *   7/2013   ............ C12Q 1/703

OTHER PUBLICATIONS

Chen et al. An integrated, self-contained microfluidic cassette for isolation, amplification, and detection of nucleic acids. Biomed Microdevices, vol. 12(4), p. 705-719, 2010.*
(Continued)

*Primary Examiner* — Young J Kim
(74) *Attorney, Agent, or Firm* — BakerHostetler

(57) ABSTRACT

Provided herein are devices for monitoring nucleic acid amplification, nucleic acid amplification monitors, methods of quantifying nucleic acid amplification, methods of identifying an unknown nucleic acid molecule, and systems for monitoring nucleic acid amplification. The disclosed devices, methods, and systems comprise at least one nuclemeter, comprising at least one sample chamber and at least one reaction-diffusion conduit in fluid communication with the chamber.

20 Claims, 17 Drawing Sheets

(52) U.S. Cl.
CPC .................. *B01L* 2200/0694 (2013.01); *B01L* 2300/0816 (2013.01); *B01L* 2300/1822 (2013.01); *B01L* 2300/1827 (2013.01); *B01L* 2300/1855 (2013.01); *B01L* 2400/0472 (2013.01); *B01L* 2400/0677 (2013.01)

(56) References Cited

U.S. PATENT DOCUMENTS

| | | | |
|---|---|---|---|
| 9,476,102 | B2 | 10/2016 | Bau et al. |
| 2001/0036634 | A1 | 11/2001 | Chow et al. |
| 2004/0110167 | A1 | 6/2004 | Gerdes et al. |
| 2008/0280285 | A1 | 11/2008 | Chen et al. |
| 2009/0186357 | A1 | 7/2009 | Mauk et al. |
| 2010/0035349 | A1 | 2/2010 | Bau et al. |
| 2013/0280698 | A1* | 10/2013 | Propper .............. G01N 33/5302 435/5 |
| 2014/0162244 | A1* | 6/2014 | Bau ........................ C12Q 1/703 435/5 |
| 2016/0002621 | A1* | 1/2016 | Nelson ................ C12N 15/1006 435/6.11 |
| 2016/0223536 | A1* | 8/2016 | Johnson ................ G01N 21/645 |

OTHER PUBLICATIONS

Chen et al., "An integrated, self-contained microfluidic cassette for isolation, amplification, and detection of nucleic acids," Biomed Microdevices, August, vol. 12, No. 4, print out pp. 1-28. (Year: 2011).*

Lee et al., "A polymer lab-on-a-chip for reverse transcription (RT)-PCR based point-of-care clinical diagnostics," Lab Chip, vol. 8, pp. 2121-2127. (Year: 2008).*

Liu et al., "An Isothermal amplification reactor with an integrated isolation membrane for point-of-care detection of infectious diseases," Analyst, May, vol. 136, No. 10, pp. 1-17. (Year: 2011).*

Kim et al., "A Disposable, Self-Contained PCR Chip," Lab Chip, vol. 9, No. 4, pp. 606-612. (Year: Feb. 2009).*

Baroud et al., "Reaction-Diffusion Dynamics: Confrontation Between Theory And Experiment In A Microfluidic Reactor", Physical Review E, Jun. 2003, 67, 1-5.

Chen et al., "An integrated, self-contained microfluidic cassette for isolation, amplification, and detection of nucleic acids", Biomed Microdevices, Aug. 2010, vol. 12, No. 4, 705-719.

Curtis et al., "Rapid detection of HIV-1 by reverse-transcription, loop-mediated isothermal amplification (RT-LAMP)", Journal of Virological Methods, 2008, 151, 264-270.

Notomi et al., "Loop-mediated isothermal amplification of DNA", Nucleic Acids Research, 2000, 28, 12, E63, 7 pages.

Tomita et al., "Loop-mediated isothermal amplification (LAMP) of gene sequences and simple visual detection of products", Nature Protocols, 2008, 3, 5, 877-882.

Zhang et al., "Survey and Summary: Miniaturized PCR Chips for Nucleic Acid Amplification and Analysis: Latest Advances and Future Trends", Nucleic Acids Research, 2007, vol. 35, No. 13, 4223-4237.

Bau, H.H, "Molecular Diagnostics at the Point of Testing", Cancer Detection and Diagnostics Technologies for Global Health, National Cancer Institute, Aug. 22-23, 2011, NIH Campus, Rockville, Maryland, pp. 27-28.

Branson, B. M., "Point-of-Care Rapid Tests for HIV Antibodies Antibodies/Patientennahe Schnelltests fur den Nachweis von HIV-Antikorpern", J. Lab. Med. Aug. 2003,27(7/8), 288-295.

Butler, S. L., "A Quantitative Assay For HIV DNA Integration In Vivo", Nature Medicine, May 2001, 7(5), 631-634.

Chen, Z., "A Microfluidic System For Saliva-Based Detection Of Infectious Diseases", Ann. NY Acad. Sci., Mar. 2007, 1098, 429-436.

Cheng, X., "Enhancing The Performance Of A Point-Of-Care CD4+ T-cell Counting Microchip Through Monocyte Depletion For HIV/AIDS Diagnostics", Lab Chip, May 2009, 9(10), 1357-1364, Published Online Feb. 4, 2009.

Curtis et al. Sequence-Specific Detection Method for Reverse Transcription, Loop-Mediated Isothermal Amplification of HIV-1. J of Med Virol. 81:966-972. 2009. [retrieved on May 9, 2012].

Dimov, I. K., "Integrated microfluidic tmRNA purification and real-time NASBA device for molecular diagnostics", Lab Chip, Oct. 2008, 8, 2071-2078.

Dineva, M.A., "Sample Preparation: A Challenge In The Development Of Point-Of-Care Nucleic Acid-Based Assays For Resource-Limited Settings", Analyst, 2007, 132, 1193-1199, Published online Oct. 1, 2007.

Donovan, et al, "HIV infection: Point-Of-Care Testing", Annuals of Pharmacotherapy, Apr. 2004, 38(4), 670-676.

Easley, C. J., "A Fully Integrated Microfluidic Genetic Analysis System With Sample-In-Answer-Out Capability", Proc. Natl. Acad. Sci. USA., Dec. 19, 2006, 103(51), 19272-19277.

Fang, X., Loop-Mediated Isothermal Amplification Integrated on Microfluidic Chips for Point-of-Care Quantitative Detection of Pathogens, Anal. Chem., Apr. 1, 2010, 82(7), 3002-3006.

Gibellini, et al, "Quantitative Detection Of Human Immunodeficiency Virus Type 1 (HIV-1) Viral Load By SYBR Green Real-Time RT-PCR Technique In HIV-1 Seropositive Patients", J. Viral. Meth., Feb. 2004, 115(2), 183-189.

Herr, A. E., Microfluidic Immunoassays As Rapid Saliva-Based Clinical Diagnostics, Proc. Natl. Acad. Sci. USA, Mar. 27, 2007, 104(13), 5268-5273.

Hill, et al, "Loop-Mediated Isothermal Ampli-Cation Assay For Rapid Detection Of Common Strains of *Escherichia coli*", J. Clin. Microbial., Jun. 2008, 46(8), 2800-2804.

International Patent Application No. PCT/US2012/025196: International Search Report and The Written Opinion dated May 29, 2012, 10 pages.

Jokerst, et al, "Integration Of Semiconductor Quantum Dots Into Nano-Bio-Chip Systems For Enumeration of CD4+ T Cell Counts At The Point-Of-Need", Lab Chip, Dec. 2008, 8(12), 2079-2090.

Kibbe, W.A., "Oligo Cale: An Online Oligonucleotide Properties Calculator", Nucleic Acids Research, 2007, 35, Web Server issue W43-W46, Published online Apr. 22, 2007. www.basic.northwestern.edu/biotools/oligocalc.html.

Kim, J., "A Disposable, Self-Contained PCR Chip", Lab Chip, Feb. 21, 2009, 9(4), 606-612.

Kim, J., "A PCR Reactor With An Integrated Alumina Membrane For Nucleic Acid Isolation", Analyst, 2010, 135, 2408-2414.

Lagally, E.T., "Fully Integrated Per-Capillary Electrophoresis Microsystem For DNA Analysis", Lab Chip, Nov. 2001, 1, 102-107.

Lee, C. S., "Multiplex PCR For The Simultaneous Detection Of Pseudorabies Virus, Porcine Cytomegalovirus, And Porcine Circovirus In Pigs", J. Viral. Methods, Jan. 2007, 139(1), 39-43.

Lee, J., "Microchip-based one step DNA extraction and real-time PCR in one chamber for rapid pathogen identification", Lab Chip, May 2006, 6(7), 886-895.

Legendre, L.A., "A Simple, Valveless Microfluidic Sample Preparation Device For Extraction And Amplification Of DNA From Nanoliter-Volume Samples", Anal. Chem., 2006, 78, 1444-1451.

Liu et al, "An Isothermal Amplification Reactor With An Integrated Isolation Membrane For Point-Of-Care Detection Of Infectious Diseases", Analyst, May 21, 2011, 136(10), 2069.

Liu, "A Disposable, Integrated Loop-Mediated Isothermal Amplification Cassette With Thermally Actuated Valves", Microfluidics and Nanofluidics, Aug. 2011, 11(2), 209-220.

Liu, C., "A Timer-Actuated Immunoassay Cassette For Detecting Molecular Markers In Oral Fluids", Lab Chip, Mar. 21, 2009, 9(6), 768-776, Published online on Dec. 5, 2008.

Liu, R. H., "Self-Contained, Fully Integrated Biochip for Sample Preparation, Polymerase Chain Reaction Amplification, and DNA Microarray Detection", Anal. Chem., Apr. 1, 2004, 76(7), 1824-1831.

Malamud, "Point Detection Of Pathogens In Oral Samples", Adv. Dent. Res., Jun. 2005, 18(1), 12-16.

Malamud, D., "Oral Diagnostic Testing For Detecting Human Immunodeficiency Virus-1 Antibodies: A Technology Whose Time Has Come", Am. J Med., Apr. 1, 1997, 102(4A), 9-14.

Malamud, D., "Saliva As A Diagnostic Fluid", Br. Med. J, Jul. 25, 1992, 305(6847), 207-208.

(56) References Cited

OTHER PUBLICATIONS

Malnati, M.S., A Universal Real-Time PCR Assay For The Quantification Of Group-M HIV-1 Proviral Load.Nature Protocols, 2008, 3(7), 1240-1248, Published online Jul. 3, 2008.
Mehta, N., "Low-Cost HIV-1 Diagnosis and Quantification in Dried Blood Spots by Real Time PCR", PLoS One, Jun. 5, 2009, 4(6), e5819.
Ochert, A. S., "Inhibitory Effect of Salivary Fluids on PCR: Potency and Removal", Genome Res., 1994, 3, 365-368.
Owen et al, "Alternative algorithms for human immunodeficiency virus infection diagnosis using tests that are licensed in the United States", J. Clin. Microbial, May 2008, 46(5), 1588-1595.
Palmer, S., "New Real-Time Reverse Transcriptase-Initiated PCR Assay with Single-Copy Sensitivity for Human Immunodeficiency Virus Type 1 RNA in Plasma", J. Clin. Microbial., Oct. 2003, 41(10), 4531-4536.
Rouet, F., "Transfer and Evaluation of an Automated, Low-Cost Real-Time Reverse Transcription-PCR Test for Diagnosis and Monitoring of Human Immunodeficiency Virus Type 1 Infection in a West African Resource-Limited Setting", J. Clin. Microbial. Jun. 2005, 43(8), 2709-2717.
Saha, B. K., "Quantitation of HIV-1 By Real-Time PCR With A Unique Fluorogenic Probe", J. Viral. Methods, Apr. 2001, 93(1-2), 33-42.
Segal, A., "Salivary Diagnostics: Enhancing Disease Detection And Making Medicine Better", Eur. J Dent. Educ., Feb. 2008, 12(Suppl 1), 22-29.
Shen, F., "Nanoliter Multiplex PCR arrays on a SlipChip", Anal. Chem., Jun. 1, 2010, 82(11), 4606-4612.
Thai et al, "Development and Evaluation of a Novel Loop-Mediated Isothermal Amplification Method for Rapid Detection of Severe Acute Respiratory Syndrome Coronavirus", J. Clin. Microbial., 2004, 42(5), 1956-1961.
Wang, J., "A Disposable Microfluidic Cassette For DNA Amplification And Detection", Lab Chip Jan. 1, 2006, 6(1), 46-53.
Westh, H., "Multiplex Real-Time PCR And Blood Culture For Identification Of Bloodstream Pathogens In Patients With Suspected Sepsis", Clin. Microbial. Infect., Jun. 2009, 15(6), 544-551.
Yager, P., "Microfluidic Diagnostic Technologies For Global Public Health", Nature, Jul. 27, 2006, 442(7101), 412-418.
Ziober, B. L., "Lab-On-A-Chip For Oral Cancer Screening And Diagnosis", Head Neck, Jan. 2008, 30, 111-121.
Liu et al, "Self Heating Cassette For Point of Care Molecular Diagnostics", Lab On Chip, 10, 1039, 2011, pp. 2686-2692.

\* cited by examiner

DEVICES AND METHODS FOR MONITORING AND QUANTIFYING NUCLEIC ACID AMPLIFICATION

CROSS-REFERENCE TO RELATED APPLICATIONS

This application is the National Stage Application of International Patent Application No. PCT/US2015/038739, filed Jul. 1, 2015, which claims priority to and the benefit of U.S. Patent Application Nos. 62/020,135, filed Jul. 2, 2014, 2014, and 62/020,484, filed Jul. 3, 2014, the disclosures of which are incorporated herein by reference in their entireties for any and all purposes.

GOVERNMENT RIGHTS

This invention was made with government support under grant numbers AI099160 and AI104418 awarded by the National Institutes of Health. The government has certain rights in the invention.

TECHNICAL FIELD

Provided herein are devices, methods, and systems for monitoring and quantifying nucleic acid amplification.

BACKGROUND

Real-time amplification and quantification of nucleic acids has revolutionized genetic research, medical diagnostics, and environmental monitoring. In the case of infectious diseases, quantification of the pathogen-load in patient specimens is critical to assess disease progression, effectiveness of drug therapy, and emergence of drug-resistance. Currently, nucleic acid quantification requires expensive instruments, such as real-time PCR machines, for continuous monitoring of fluorescence emission from intercalating dye or molecular beacon probes. Although enzymatic amplification products can be detected without an instrument with lateral flow strips, this method suffers from low accuracy and low sensitivity.

Thus, there is a need for devices and methods providing low-cost, instrument-free, monitoring and end-point quantification of target nucleic acids undergoing enzymatic amplification. The invention is directed to these and other important needs.

SUMMARY

Disclosed are devices, methods, and systems for low-cost, reaction-diffusion based, instrument-free, monitoring and end-point quantification of target nucleic acids undergoing enzymatic amplification. The target concentration is estimated from a length measurement along a reaction-diffusion-conduit. Exemplary uses of the disclosed devices, methods, and systems include on-site or high throughput applications and the identification of gene expression profiles.

Provided herein are devices for monitoring nucleic acid amplification comprising a nuclemeter comprising a sample chamber and at least one reaction-diffusion conduit in fluid communication with the chamber. In some embodiments, each of the chamber and the conduit hold a blend of reactants for nucleic acid amplification. In other embodiments, each of the chamber and the conduit are capable of holding a blend of reactants for nucleic acid amplification.

Also disclosed are nucleic acid amplification monitors comprising a substrate and, on or forming a part of the substrate, a plurality of nuclemeters, each nuclemeter comprising a sample chamber and at least one reaction-diffusion conduit in fluid communication with the sample chamber; each of the sample chamber and the conduit being capable of holding a blend of reactants for nucleic acid amplification.

Methods of quantifying nucleic acid amplification are also provided herein, said methods comprising amplifying a sample comprising a nucleic acid molecule in any of the devices or the nucleic acid amplification monitors disclosed herein to generate an amplified nucleic acid molecule and measuring a reaction-diffusion length of said amplified nucleic acid molecule through the one or more conduits, wherein reaction-diffusion length is proportional to the number of nucleic acid copies in the sample and time.

Further disclosed are methods of identifying an unknown nucleic acid molecule, comprising amplifying a sample having an unknown nucleic acid molecule in any of the devices or nucleic acid amplification monitors disclosed herein, wherein each of the at least one conduits contain a plurality of primers specific for a different known nucleic acid molecule, and measuring a reaction-diffusion length within the reaction-diffusion conduit, wherein the presence of the reaction-diffusion length indicates that the sample having an unknown nucleic acid molecule comprises the known nucleic acid molecule to which the primers in the at least one conduit are specific and the extent of the reaction-diffusion length within the conduit indicates the number of the unknown nucleic acid molecules in the sample.

Further disclosed are systems for monitoring nucleic acid amplification comprising a nuclemeter comprising a sample chamber, at least one reaction-diffusion conduit in fluid communication with the sample chamber, each of the sample chamber and the conduit being capable of holding a blend of reactants for nucleic acid amplification, an optical imager, and a heat source.

The general description and the following detailed description are exemplary and explanatory only and are not restrictive of the invention, as defined in the appended claims. Other aspects of the present invention will be apparent to those skilled in the art in view of the detailed description as provided herein.

BRIEF DESCRIPTION OF THE DRAWINGS

The summary, as well as the following detailed description, is further understood when read in conjunction with the appended drawings. For the purpose of illustrating the disclosed devices, methods, and systems, there are shown in the drawings exemplary embodiments of the devices, methods, and systems; however, the invention is not limited to the specific devices, methods, and systems disclosed. In the drawings:

FIGS. 1A-1E, represent the design and operation of an exemplary nuclemeter for HIV viral load testing. (a) A schematic depiction of the cross-section of the nuclemeter, consisting of a sample well and a reaction-diffusion microconduit. (b) An illustration of the nuclemeter's operation. Initially, only the sample chamber contains the nucleic acid template (top). The template amplifies and diffuses into the reaction-conduit, where it continues to amplify at 62.5° C. (middle). $X_F$ indicates the position of the reaction front that propagates with a constant velocity ($v_0$) (bottom). (c) A photograph of a plastic chip housing four nuclemeters. (d) Fluorescence images of the reaction-diffusion conduits of four nuclemeters containing $10^4$, $10^3$, $10^2$, and 0 (negative control) HIV-1 RNA templates at various times after the start of incubation. (e) Four nuclemeters each containing 100 HIV-1 RNA templates to illustrate reproducibility.

FIGS. 2A-2I, represent exemplary experimental data and theoretical predictions of nuclemeter's performance. (a) Normalized emission intensity $\hat{c}=c/c_{max}$ as a function of position along the reaction-diffusion conduit at various times. The solid lines and symbols correspond, respectively, to predictions and experimental data. The number of target molecules is $10^3$ copies. (b) Normalized emission intensity $\hat{c}$ as a function of time at positions x=1.2, 1.8, and 2.4 mm along the length of the conduit. The solid lines and symbols correspond, respectively, to the predictions and experimental data. The number of target molecules is $10^3$ copies. (c) The experimental rate of the reaction $$\left(-\frac{\partial \hat{c}}{\partial t}\right)_{exp}$$

as a function of position (x) at various times. (d) The measured width of the reaction-rate peak at midheight $\Lambda_{exp}$ as a function of time. (e) The measured position of the reaction front $X_{F,\ exp}$ as a function of time for various template concentrations (error bars=standard deviation (s.d.); n=3; $R^2$=0.998). (f) The intercept ($t_{0,\ exp}$) of the line in FIG. 2e and the threshold time $C_t$ of real-time RT-LAMP curves as functions of the number of templates (error bars=s.d.; n=3; $R^2$=0.99). (g) $X_{F,\ exp}$-$X_{F,exp}^{(3)}$ as a function of the template number at various times t (error bars=s.d.; $R^2$=0.99, n=15). (h) The predicted position of the reaction front ($X_{F,\ th}$) as a function of time for various numbers of templates. (i) The predicted intercept ($t_{0,\ th}$) of the asymptotes in FIG. 2h as a function of template number.

Figure 3:
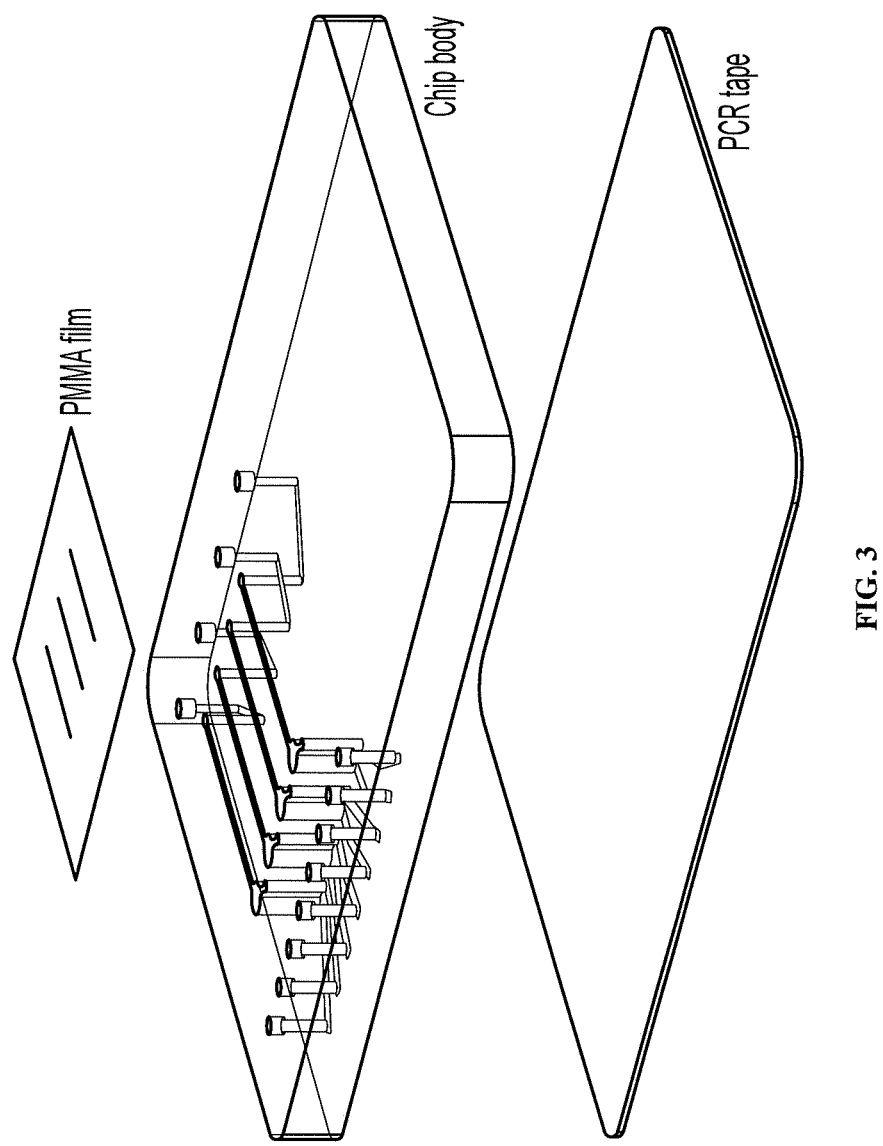

FIG. 3 represents an exploded view of an exemplary nuclemeter chip consisting of three layers: a top PMMA film, a PMMA chip body, and a bottom PCR Sealers™ tape. The various features of the chip body were milled with a CNC machine.

Figure 4:
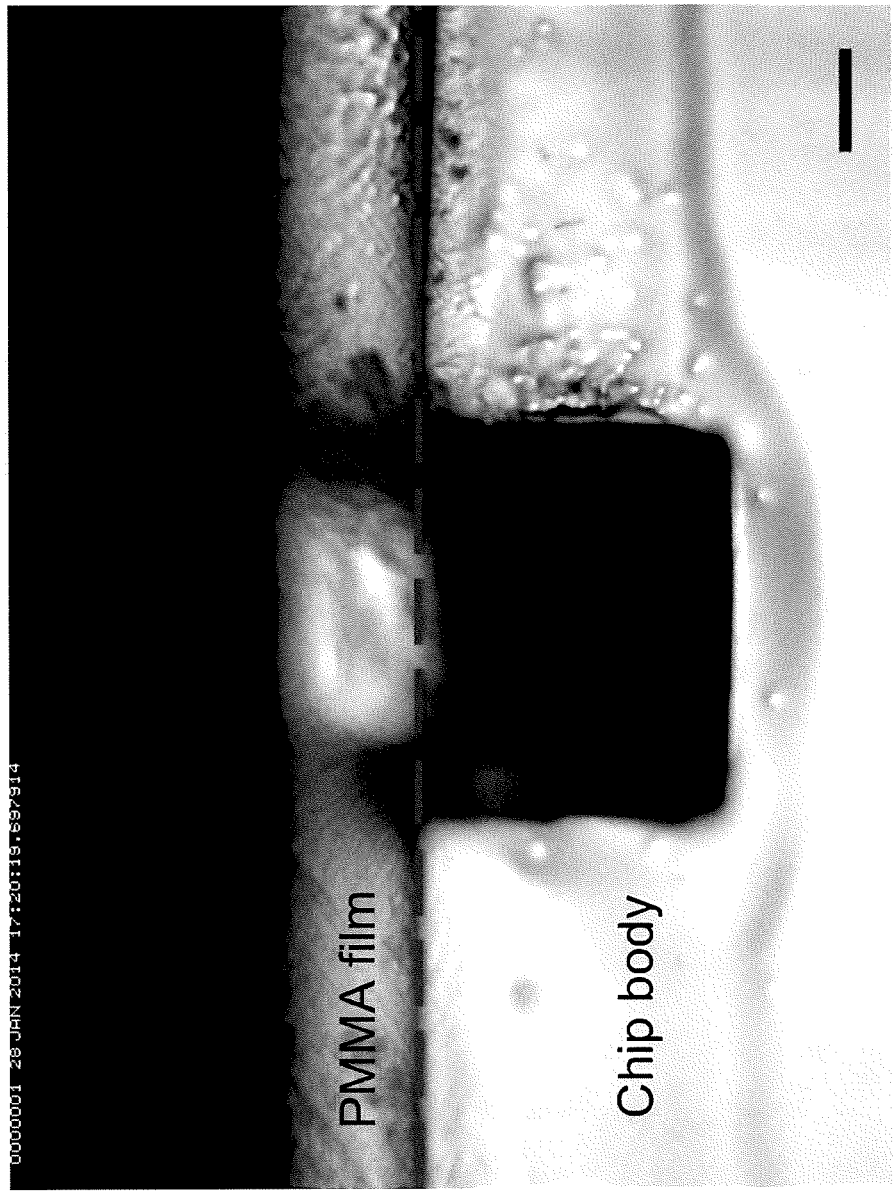

FIG. 4 represents a micrograph of the reaction-diffusion micro-conduit's cross-section. The dashed line indicates the interface between the PMMA film and the PMMA chip body.

Figure 5:
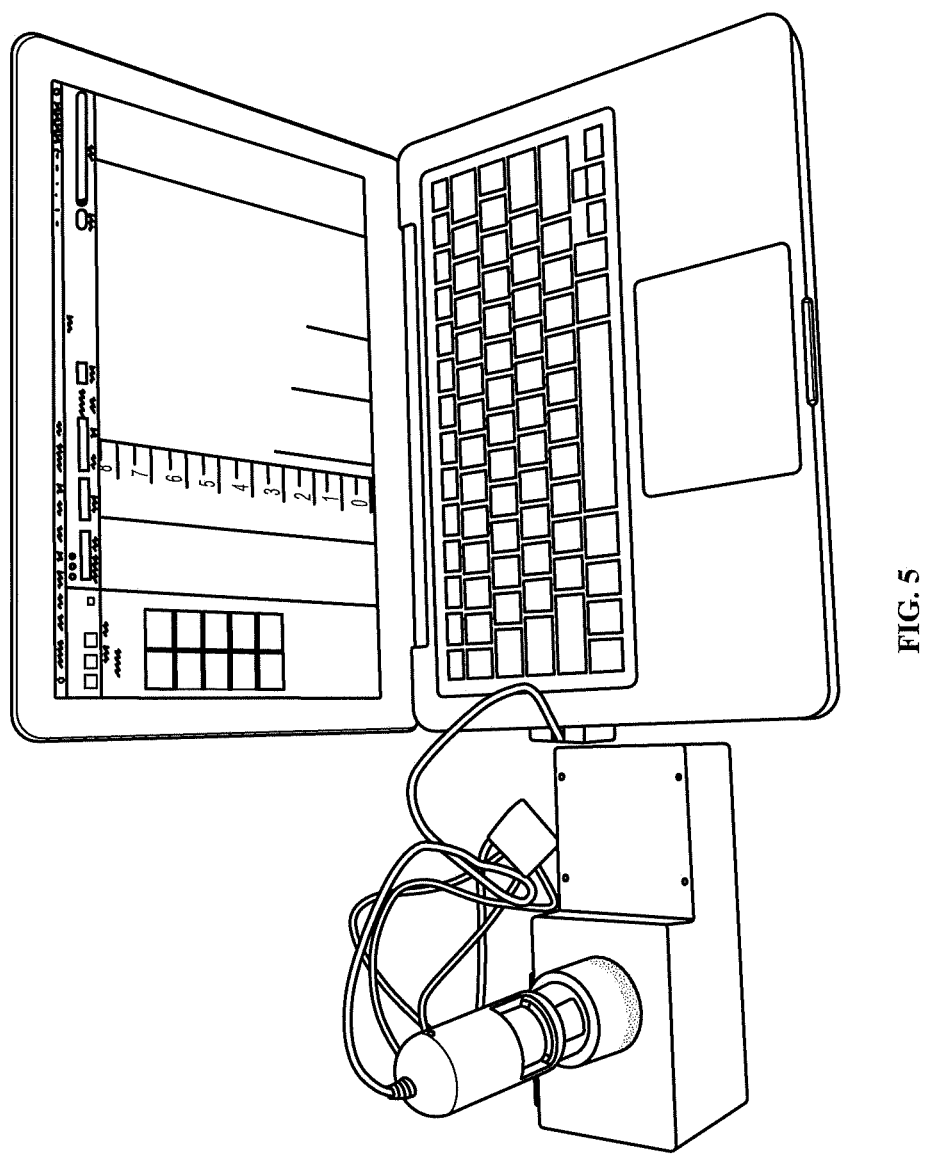

FIG. 5 represents an exemplary experimental setup for the nuclemeter chip. The portable processor includes a USB-based, fluorescence microscope (AM4113T-GFBW Dino-Lite Premier, AnMo Electronics, Taipei, Taiwan). The processor can be powered either with four AA batteries or by grid power. The fluorescence image of the nuclemeters can be directly displayed on the computer screen. The USB microscope can be replaced with LED illumination and a smartphone camera or other imaging devices.

Figure 6:
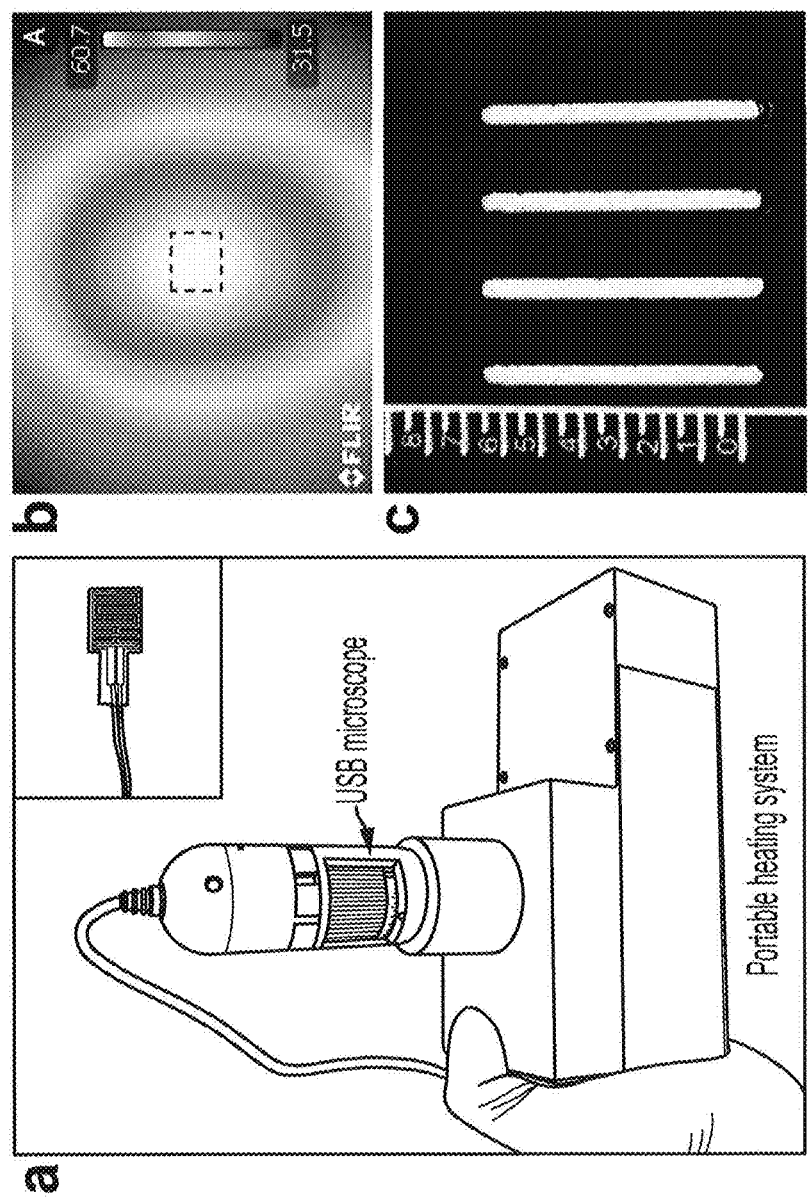

FIG. 6, comprising FIGS. 6A-6C, represent an exemplary portable, processor for RT-LAMP amplification and detection. (a) A photograph of the processor. Inset: a flexible, polyimide-based, thin film heater (HK5572R7.5L23A, Minco Products, Inc., Minneapolis, MN). The heater can be replaced with an exothermic reaction chamber (b) A thermograph of the nuclemeter chip's surface taken with an infrared camera T360 (FLIR Systems, Wilsonville, USA). The four reaction-diffusion reactors are located within the dashed square. (c) A mask made with black 3M Scotch electrical tape to block background emission. The mask is equipped with a ruler to assist in determining the position of the reaction front ($X_F$).

Figure 7:
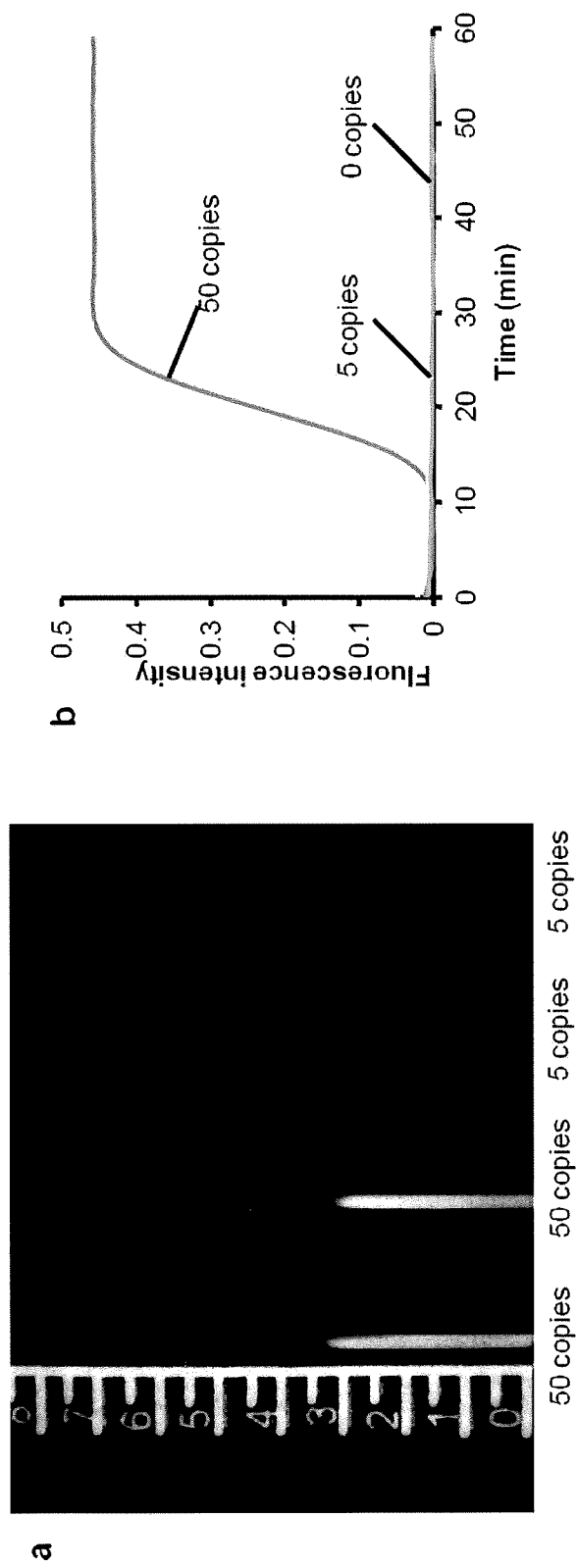

FIG. 7, comprising FIGS. 7A-7B represent an evaluation of the limits of detection of an examplary nuclemeter and benchtop, "tubed-based" LAMP. (a) A representative, end-point fluorescent image of the nuclemeter chip with 50 copies (lanes 1 and 2) and 5 copies (lanes 3 and 4) of target HIV RNA molecules. (b) Real-time, benchtop monitoring of RT-LAMP amplification of HIV viral RNA with 50, 5, and 0 (negative control) target RNA copies per tube. Both the nuclemeter and the real time machine detected successfully 50 target molecules and failed to detect 5 target molecules.

Figure 8:
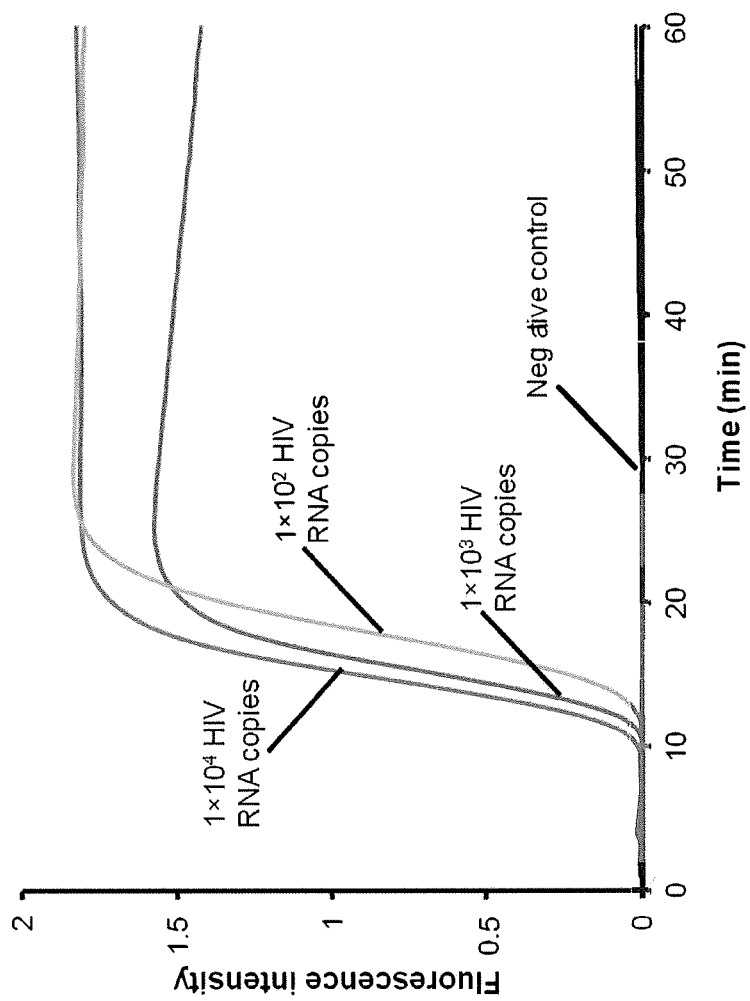

FIG. 8, represents real-time, benchtop monitoring of RT-LAMP amplification of HIV viral RNA with $10^4$, $10^3$, $10^2$, and 0 (negative control) target RNA molecules per tube on the benchtop PCR machine. The tubes include 0.04% HPMC to replicate the conditions in the nuclemeter chip.

Figure 9:
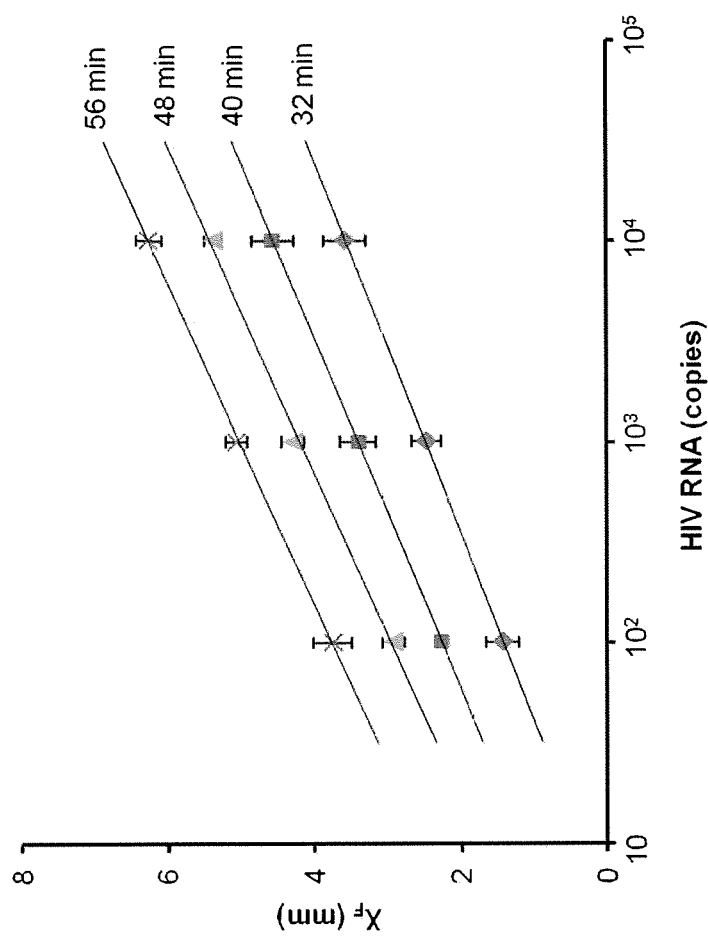

FIG. 9 represents the position of the reaction front ($X_F$) as a function of the number of target molecules (n=3) at times (from bottom to top) 32, 40, 48 and 56 min after the start of incubation.

Figure 10:
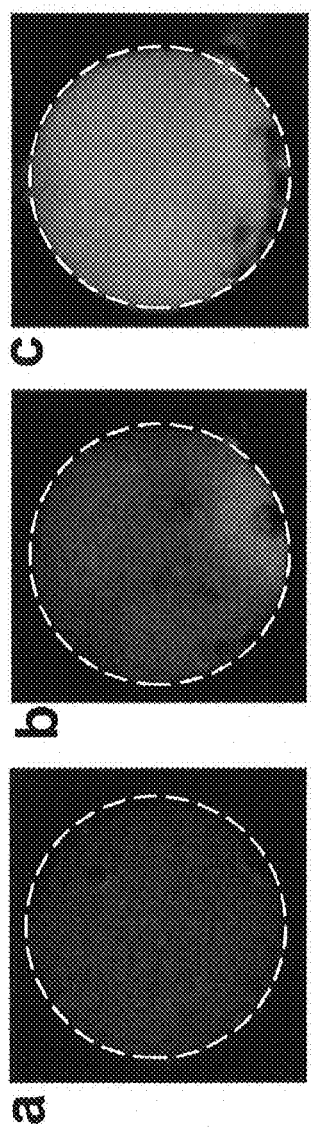
Figure 10:
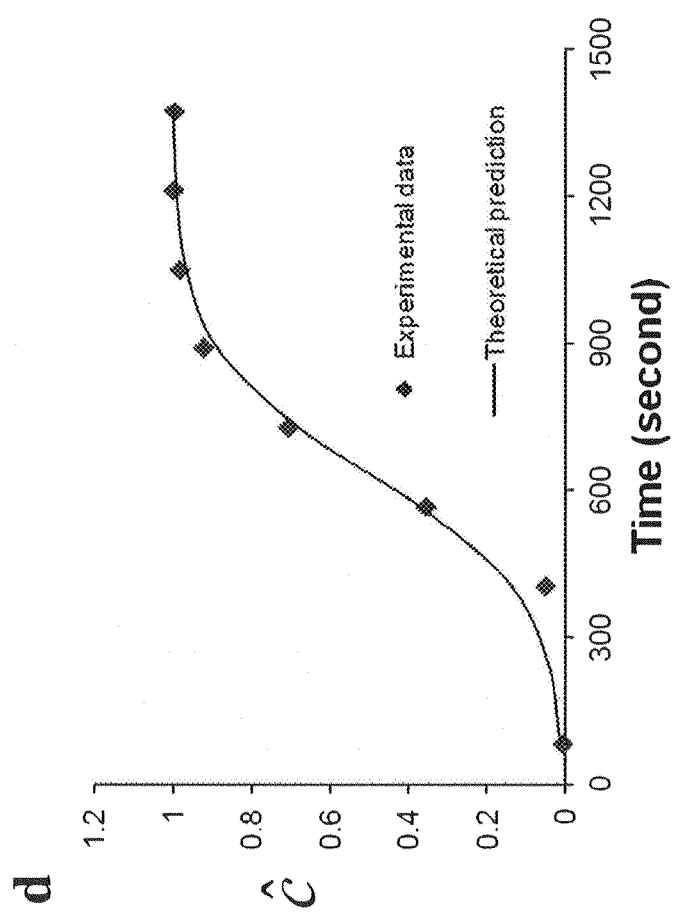

FIG. 10, comprising FIGS. 10A-10D, represent an exemplary nuclemeter's sample well emission (a) before RT-LAMP amplification, (b) shortly after the onset of amplification, and (c) at saturation of amplification. The number of target molecules is $10^3$ copies. (d) a fluorescent emission from the exemplary nuclemeter's sample chamber as a function of the time. The solid line and the symbols correspond, respectively, to the best fit line based on equation 4 and the experimental data. The number of target molecules is $10^3$ copies.

Figure 11:
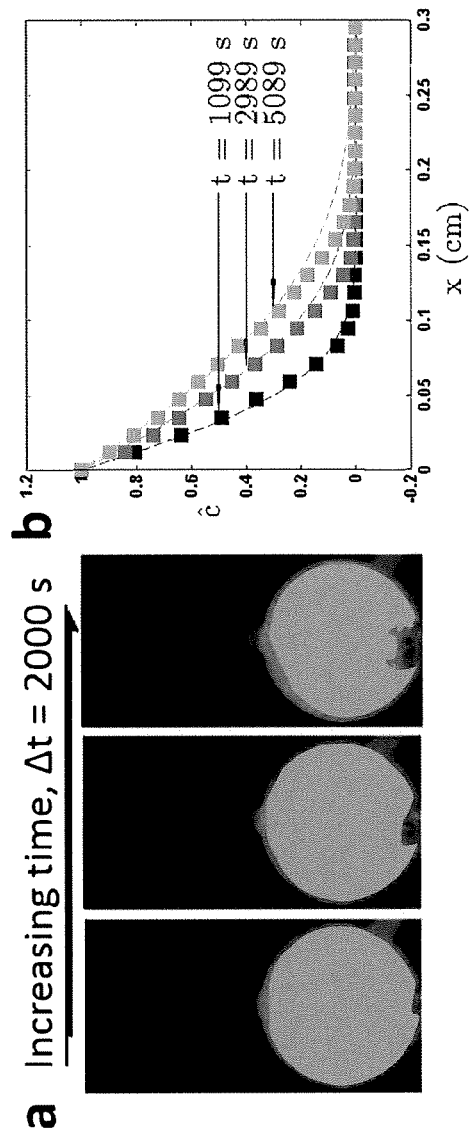

FIG. 11, comprising FIGS. 11A-11B, represents: (a) the concentration distribution of the labeled primers in the reaction-diffusion conduit at various times in the absence of an amplification reaction. (b) The emission intensity (normalized with the initial concentration) as a function of position at various times. The lines correspond to theoretical predictions and the symbols to the experimental data (with optimal estimate for the diffusion coefficient).

Figure 12:
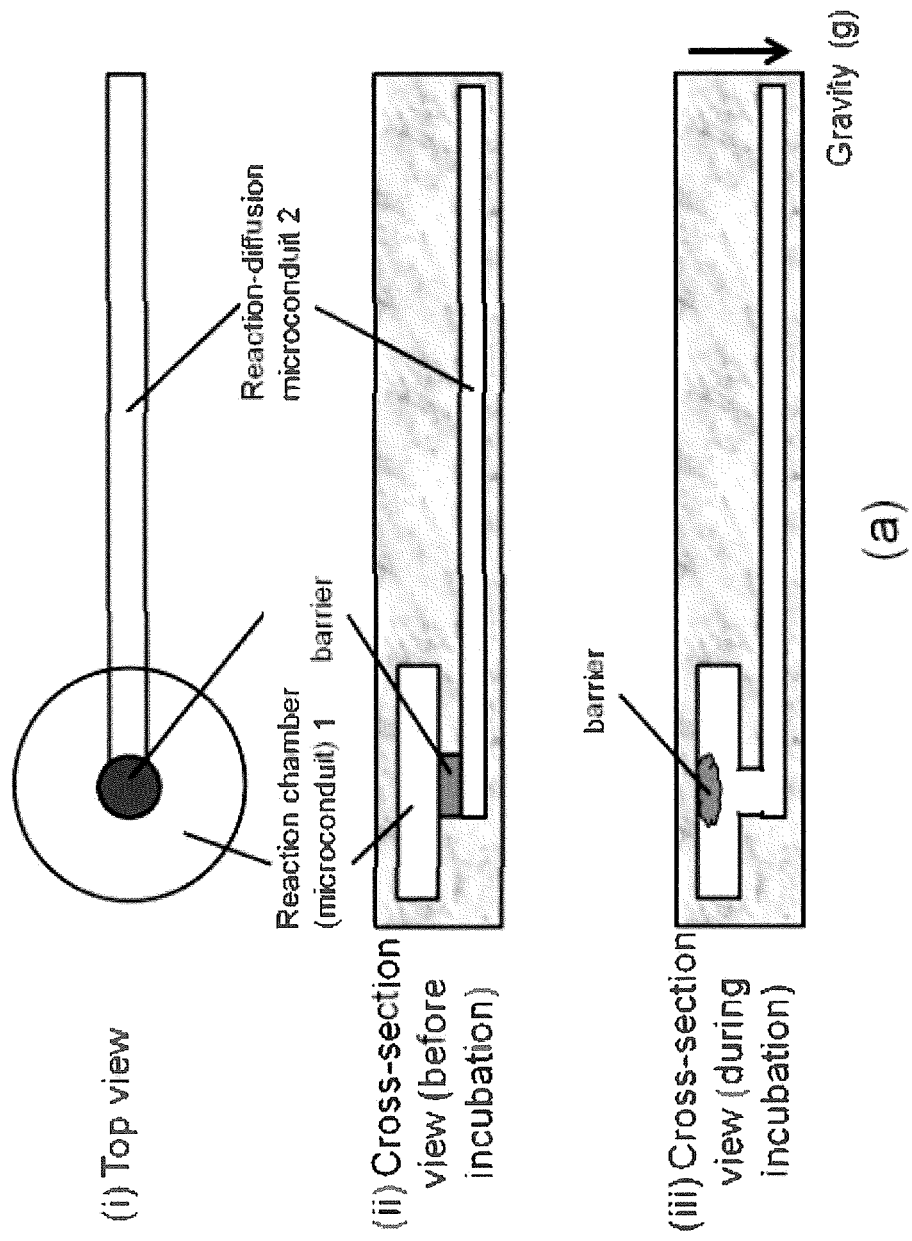
Figure 12:
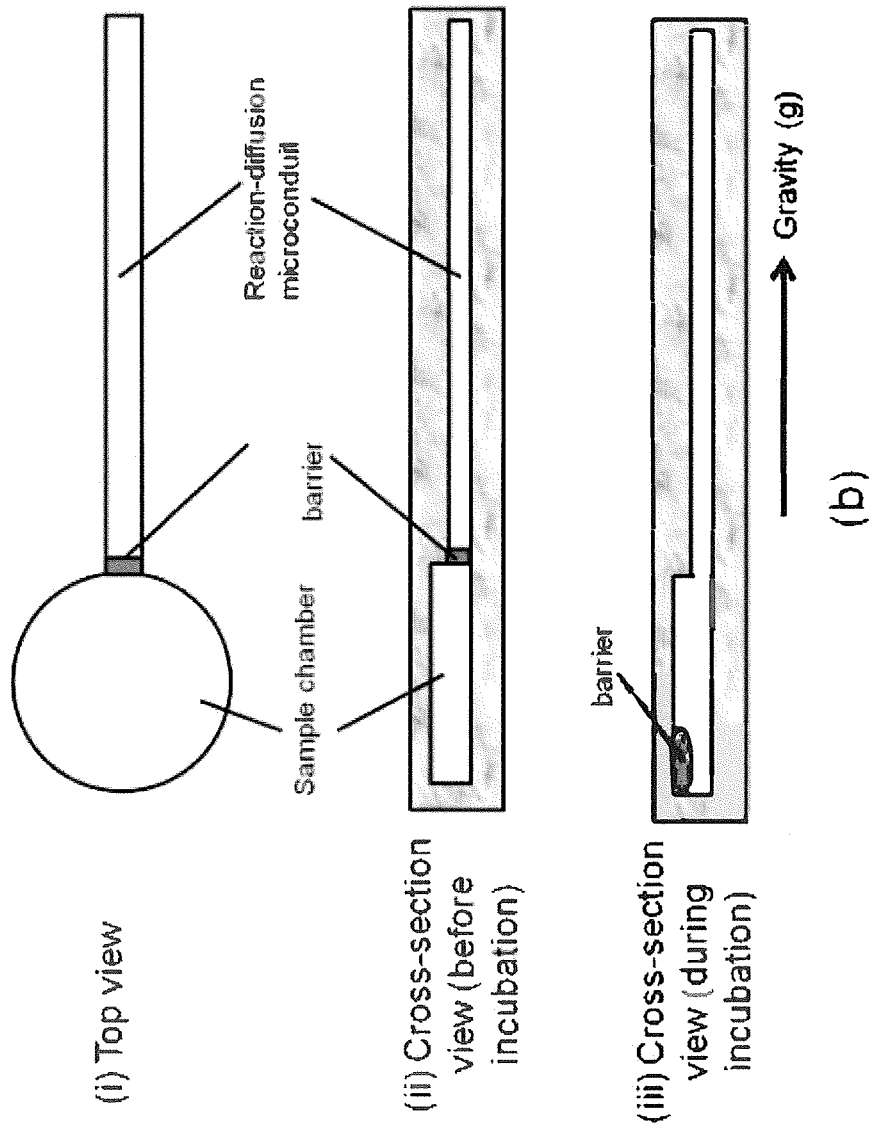

FIG. 12, comprising FIGS. 12A-12B, illustrates a schematic depiction of an exemplary nuclemeter in which the sample chamber and the reaction-diffusion conduits are separated with a barrier consisting of a phase change material. (i) represents a top view with the barrier in place; (ii) represents a side-view with the barrier in place; (iii) represents a side view after the barrier had dissolved, melted, moved, been removed, etc. to allow hydraulic communications between the sample chamber and the reaction-diffusion conduit. Furthermore, the sample chamber contains an optional membrane for the isolation of nucleic acids. The device enables multi-stage amplification with one amplicon being amplified in the sample chamber and the other in the diffusion-reaction conduit.

Figure 13:
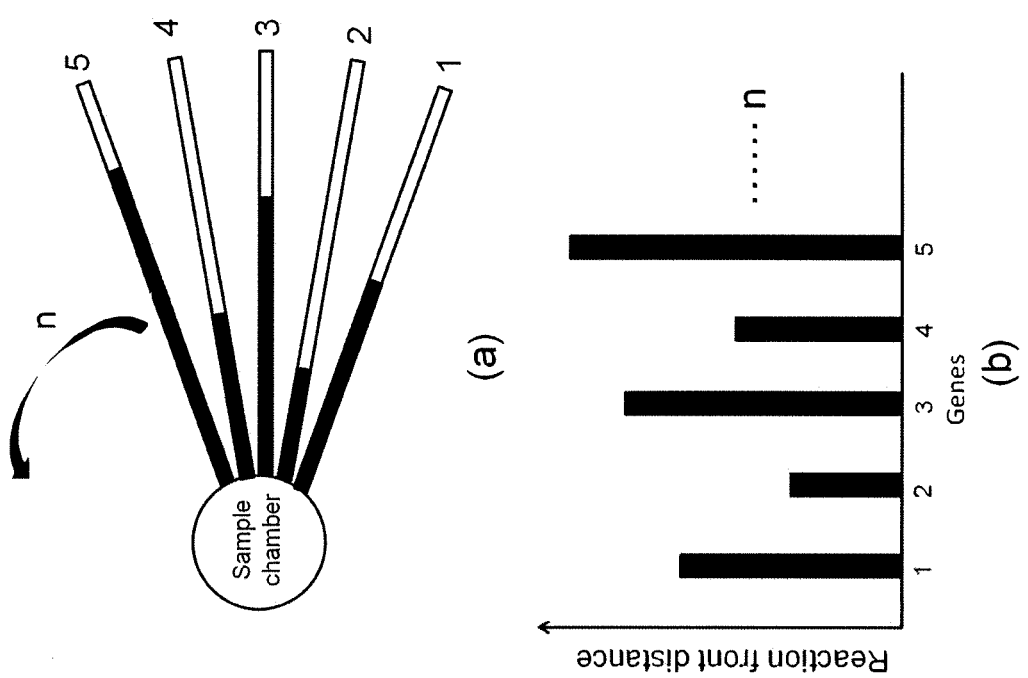

FIG. 13, comprising FIGS. 13A-13B, illustrates a schematic depiction of an exemplary nuclemeter comprising a single sample chamber and multiple reaction-diffusion conduits, each customized to amplify a different nucleic acid. The relative quantities of the various nucleic acids are determined from the relative lengths of the reacted regions, as indicated by the fluorescence emission, in the reaction-diffusion columns, enabling the identification of, among other things, a gene expression profile or bacterial flora.

Figure 14:
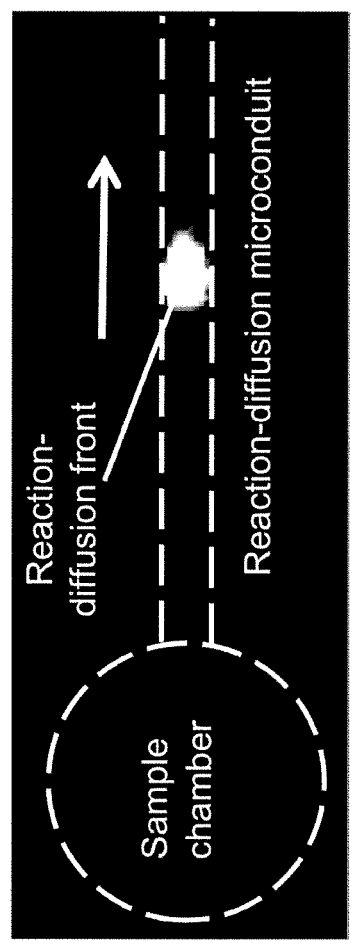

FIG. 14 is an image of an exemplary nuclemeter utilizing bioluminescent assay for real-time recording of the position of the reaction front. The luminescence blob propagates along the conduit and indicates the instantaneous position of the reaction front. The target in this particular assay is HIV.

DETAILED DESCRIPTION OF ILLUSTRATIVE EMBODIMENTS

The disclosed devices, methods, and systems may be understood more readily by reference to the following detailed description taken in connection with the accompanying figures, which form a part of this disclosure. It is to be understood that the disclosed devices, methods, and systems are not limited to the specific devices, methods, and systems described and/or shown herein, and that the terminology used herein is for the purpose of describing particular embodiments by way of example only and is not intended to be limiting of the claimed devices, methods, and systems.

Unless specifically stated otherwise, any description as to a possible mechanism or mode of action or reason for improvement is meant to be illustrative only, and the disclosed devices, methods, and systems are not to be constrained by the correctness or incorrectness of any such suggested mechanism or mode of action or reason for improvement.

Reference to a particular numerical value includes at least that particular value, unless the context clearly dictates otherwise. When a range of values is expressed, another embodiment includes from the one particular value and/or to the other particular value. Further, reference to values stated in ranges include each and every value within that range. All ranges are inclusive and combinable.

When values are expressed as approximations, by use of the antecedent "about," it will be understood that the particular value forms another embodiment.

It is to be appreciated that certain features of the disclosed devices, methods, and systems which are, for clarity, described herein in the context of separate embodiments, may also be provided in combination in a single embodiment. Conversely, various features of the disclosed devices, methods, and systems that are, for brevity, described in the context of a single embodiment, may also be provided separately or in any subcombination.

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

As used herein, the term "about" is meant to encompass variations of ±20% or less, variations of 10% or less, variations of ±5% or less, variations of ±1% or less, variations of ±0.5% or less, or variations of ±0.1% or less from the specified value.

As used herein, the term "fluid communication" refers to ability of liquids to diffuse between the sample chamber and the at least one reaction-diffusion conduit. For example, nucleic acid molecules diffuse from the sample chamber into the at least one reaction-diffusion conduit.

As used herein, "nucleic acid amplification" includes any technique used to detect nucleic acids by amplifying (generating numerous copies of) the target molecules in the sample. Suitable nucleic acid amplification techniques include, but are not limited to, loop-mediated isothermal amplification (LAMP), reverse transcription-loop mediated isothermal amplification (RT-LAMP), or polymerase chain reaction.

As used herein, the term "nuclemeter" refers to a reaction-diffusion device for monitoring and quantitative detection of amplified nucleic acid molecules based on the position of the reaction front. Each nuclemeter comprises at least one sample chamber and at least one reaction-diffusion conduit in fluid communication with the sample chamber.

"Target" refers to a sequence, or partial sequence, of a nucleic acid of interest. "Target" and "nucleic acid molecule" are used interchangeably herein.

Devices for Monitoring Nucleic Acid Amplification

Provided herein are devices for monitoring nucleic acid amplification comprising a nuclemeter. The nuclemeter comprises a sample chamber and at least one reaction-diffusion conduit in fluid communication with the chamber. In some embodiments, each of the chamber and the at least one reaction-diffusion conduit hold a blend of reactants for nucleic acid amplification. In other embodiments, each of the chamber and the at least one reaction-diffusion conduit are capable of holding a blend of reactants for nucleic acid amplification. The sample chamber may also serve as a nucleic acid amplification reactor.

In some embodiments, the device for monitoring nucleic acid amplification can comprise a nuclemeter comprising a sample chamber and at least one reaction-diffusion conduit in fluid communication with the sample chamber, each of the sample chamber and the conduit being capable of holding a blend of reactants for nucleic acid amplification.

In other embodiments, the device for monitoring nucleic acid amplification can comprise a nuclemeter comprising a sample chamber and at least one reaction-diffusion conduit in fluid communication with the sample chamber, each of the sample chamber and the conduit holding a blend of reactants for nucleic acid amplification.

The sample chamber and diffusion-reaction conduit can be separated with a barrier. The barrier can be configured to block passage of reactants between the sample chamber and the reaction-diffusion conduit during sample introduction, nucleic acid isolation, etc. and can be configured to allow passage of reactants between the sample chamber and the reaction-diffusion conduit at a specified time or in response to an event. In some embodiments, the barrier can be removable. In some aspects, for example, the barrier can be physically removed from the nuclemeter. In some embodiments, the barrier can be degradable. For example, the barrier can be composed of, or can comprise, a material that degrades. In some embodiments, the barrier can be dissolvable. For example, the barrier can be composed of a material that dissolves in solution. Exemplary materials that dissolve in solution include, for example, salt. In some embodiments, the barrier can be capable of being melted. For example, the barrier can be composed of, or can comprise, a phase change material that melts, or partially melts, at a certain temperature. For example, the barrier can melt and move through the action of surface tension (capillary) forces or buoyancy or combination thereof, thereby allowing diffusion between the sample chamber and the reaction diffusion conduit. In some embodiments, the barrier can be movable. For example, the barrier can be configured to open or otherwise allow passage of sample between the sample chamber and the reaction diffusion conduit in response to a mechanical force or various means of actuation. For example, the actuator may consist of bi-metal or shape memory alloy that alters shape in response to temperature variations.

The barrier can allow for a two-step or nested-like amplification. For example, two different amplification reactions can be run; one in the sample chamber and one in the reaction-diffusion conduit. The reaction in the sample chamber can, for example, amplify nucleic acid molecules nonspecifically. Once the reaction in the sample chamber is complete, the barrier can be removed, dissolved, degraded, melted, etc. allowing the amplified nucleic acid molecules to diffuse into the reaction-diffusion conduit, which can contain primers for a specific nucleic acid molecule. Within the reaction-diffusion conduit, specific nucleic acid molecules will then be amplified. The two reactions can operate with different enzymes, temperatures, etc.

The sample chamber can have a size and shape suitable for containing a nucleic acid amplification reaction. For example, the cross-section of the sample chamber can have a variety of suitable shapes, including, but not limited to, square, rectangular, triangular, pentagonal, hexagonal, heptagonal, octagonal, nonagonal, decagonal, round, or elliptical.

The bottom of the sample chamber can be flat, substantially flat, conical, round, substantially round, or pointed or contain depressions, for example, for the purpose of storing reagents needed for the amplification process.

In some embodiment the sample chamber can be a droplet, which can be manipulated to make contact with the reaction-diffusion conduit. Numerous techniques are known for manipulating droplets including, but not limited to, electrowetting, thermal gradients, solute gradients, conduit geometry such as taper, or any combination thereof. For example, in some embodiments, a droplet comprising the reactant mixture and nucleic acid sample can be placed onto a surface containing a plurality of electrodes. An electric field can be applied to the surface resulting in migration of the droplet towards (or away from) the reaction-diffusion conduit. The electric field can be applied until the droplet makes contact, such as a hydraulic connection, with the reaction-diffusion conduit. As amplification progresses, the amplified nucleic acid sample can diffuse into the reaction-diffusion conduit. In some embodiments, the droplet is the sample chamber. In other embodiments, the droplet is placed within the sample chamber. In some embodiments, the droplet can be encased in oil. In some embodiments, the droplet can be produced by a microfluidic device.

The sample chamber, when used for nucleic acid amplification, will have a size suitable for a containing a nucleic acid amplification reaction. Suitable sizes include sample chambers having a volume of from about 0.1 µl to about 300 µl. In one embodiment, the sample chamber has a volume of about 0.1 µl. In one embodiment, the sample chamber has a volume of about 0.5 µl. In one embodiment, the sample chamber has a volume of about 1 µl. In one embodiment, the sample chamber has a volume of about 10 µl. In one embodiment, the sample chamber has a volume of about 20 µl. In one embodiment, the sample chamber has a volume of about 50 µl. In one embodiment, the sample chamber has a volume of about 100 µl. In one embodiment, the sample chamber has a volume of about 150 µl. In one embodiment, the sample chamber has a volume of about 200 µl. In one embodiment, the sample chamber has a volume of about 250 µl. In one embodiment, the sample chamber has a volume of about 300 µl. In some embodiments, the sample chamber has a volume greater than 300 µl.

The sample chamber can be from about 0.1 µl to about 300 µl in volume. In some aspects, the sample chamber can be from about 0.1 µl to about 250 µl in volume. The sample chamber can be from about 0.1 µl to about 200 µl in volume. The sample chamber can be from about 0.1 µl to about 150 µl in volume. The sample chamber can be from about 0.1 µl to about 100 µl in volume. The sample chamber can be from about 0.1 µl to about 50 µl in volume. The sample chamber can be from about 10 µl to about 300 µl in volume. The sample chamber can be from about 10 µl to about 200 µl in volume. The sample chamber can be from about 10 µl to about 150 µl in volume. The sample chamber can be from about 10 µl to about 100 µl in volume. The sample chamber can be from about 10 µl to about 50 µl in volume. In some aspects, the sample chamber can be from about 25 µl to about 300 µl in volume. The sample chamber can be from about 50 µl to about 300 µl in volume. The sample chamber can be from about 75 µl to about 300 µl in volume. The sample chamber can be from about 100 µl to about 300 µl in volume. The sample chamber can be from about 125 µl to about 300 µl in volume. The sample chamber can be from about 150 µl to about 300 µl in volume. The sample chamber can be from about 175 µl to about 300 µl in volume. The sample chamber can be from about 200 µl to about 300 µl in volume. The sample chamber can be from about 225 µl to about 300 µl in volume. The sample chamber can be from about 250 µl to about 300 µl in volume. The sample chamber can be from about 275 µl to about 300 µl in volume.

The height of the sample chamber can be from about 0.05 mm to about 10 mm. The height of the sample chamber can be from about 0.1 mm to about 9 mm. The height of the sample chamber can be from about 0.2 mm to about 8 mm. The height of the sample chamber can be from about 0.3 mm to about 7 mm. The height of the sample chamber can be from about 0.4 mm to about 6 mm. The height of the sample chamber can be from about 0.5 mm to about 5 mm. The height of the sample chamber can be from about 0.6 mm to about 4 mm. The height of the sample chamber can be from about 0.7 mm to about 3 mm. The height of the sample chamber can be from about 0.8 mm to about 2 mm. The height of the sample chamber can be from about 0.9 mm to about 1 mm.

In some aspects, the height of the sample chamber can be about 0.05 mm. In some aspects, the height of the sample chamber can be about 0.1 mm. In some aspects, the height of the sample chamber can be about 0.2 mm. In some aspects, the height of the sample chamber can be about 0.3 mm. In some aspects, the height of the sample chamber can be about 0.4 mm. In some aspects, the height of the sample chamber can be about 0.5 mm. In some aspects, the height of the sample chamber can be about 0.6 mm. In some aspects, the height of the sample chamber can be about 0.7 mm. In some aspects, the height of the sample chamber can be about 0.8 mm. In some aspects, the height of the sample chamber can be about 0.9 mm. In some aspects, the height of the sample chamber can be about 1 mm. In some aspects, the height of the sample chamber can be about 2.5 mm. In some aspects, the height of the sample chamber can be about 5 mm. In some aspects, the height of the sample chamber can be about 7.5 mm. In some aspects, the height of the sample chamber can be about 10 mm.

The width of the sample chamber can be from about 0.05 mm to about 5 mm. The width of the sample chamber can be from about 0.1 mm to about 4 mm. The width of the sample chamber can be from about 0.2 mm to about 3 mm. The width of the sample chamber can be from about 0.3 mm to about 2 mm. The width of the sample chamber can be from about 0.4 mm to about 1 mm. The width of the sample chamber can be from about 0.5 mm to about 0.9 mm. The width of the sample chamber can be from about 0.6 mm to about 0.8 mm.

The width of the sample chamber can be about 0.05. The width of the sample chamber can be about 0.1 mm. The width of the sample chamber can be about 0.2 mm. The width of the sample chamber can be about 0.3 mm. The width of the sample chamber can be about 0.4 mm. The width of the sample chamber can be about 0.5 mm. The width of the sample chamber can be from 0.6 mm. The width of the sample chamber can be about 0.7. The width of the sample chamber can be about 0.8 mm. The width of the sample chamber can be about 0.9 mm. The width of the sample chamber can be about 1 mm. The width of the sample chamber can be about 2 mm. The width of the sample chamber can be about 3 mm. The width of the sample chamber can be about 4 mm. The width of the sample chamber can be about 2 mm. The width of the sample chamber can be about 5 mm.

The length of the reaction-diffusion conduit can be from about 0.05 mm to about 100 mm. The length of the reaction-diffusion conduit can be from about 0.05 mm to about 75 mm. The length of the reaction-diffusion conduit can be from about 0.05 mm to about 50 mm. The length of the reaction-diffusion conduit can be from about 0.05 mm to about 25 mm. The length of the reaction-diffusion conduit can be from about 0.05 mm to about 10 mm. The length of the reaction-diffusion conduit can be from about 0.05 mm to about 5 mm. The length of the reaction-diffusion conduit can be from about 0.05 mm to about 2.5 mm. The length of the reaction-diffusion conduit can be from about 0.05 mm to about 1 mm. The length of the reaction-diffusion conduit can be from about 0.05 mm to about 0.5 mm.

The length of the reaction-diffusion conduit can be about 100 mm. The length of the reaction-diffusion conduit can be about 75 mm. The length of the reaction-diffusion conduit can be about 50 mm. The length of the reaction-diffusion conduit can be about 25 mm. The length of the reaction-diffusion conduit can be about 10 mm. The length of the reaction-diffusion conduit can be about 5 mm. The length of the reaction-diffusion conduit can be about 2.5 mm. The length of the reaction-diffusion conduit can be about 1 mm. The length of the reaction-diffusion conduit can be about 0.5 mm.

The height of the reaction-diffusion conduit can be from about 0.1 µm to about 1 mm. The height of the reaction-diffusion conduit can be from about 0.1 µm to about 750 µm. The height of the reaction-diffusion conduit can be from about 0.1 µm to about 500 µm. The height of the reaction-diffusion conduit can be from about 0.1 µm to about 250 µm. The height of the reaction-diffusion conduit can be from about 0.1 µm to about 100 µm. The height of the reaction-diffusion conduit can be from about 0.1 µm to about 50 µm. The height of the reaction-diffusion conduit can be from about 0.1 µm to about 25 µm. The height of the reaction-diffusion conduit can be from about 0.1 µm to about 10 µm. The height of the reaction-diffusion conduit can be from about 0.1 µm to about 5 µm. The height of the reaction-diffusion conduit can be from about 0.1 µm to about 1 µm. The height of the reaction-diffusion conduit can be from about 0.1 µm to about 0.5 µm.

The height of the reaction-diffusion conduit can be about 1 mm. The height of the reaction-diffusion conduit can be about 750 µm. The height of the reaction-diffusion conduit can be about 500 µm. The height of the reaction-diffusion conduit can be about 250 µm. The height of the reaction-diffusion conduit can be about 100 µm. The height of the reaction-diffusion conduit can be about 50 µm. The height of the reaction-diffusion conduit can be about 25 µm. The height of the reaction-diffusion conduit can be about 10 µm. The height of the reaction-diffusion conduit can be about 5 µm. The height of the reaction-diffusion conduit can be about 1 µm. The height of the reaction-diffusion conduit can be about 0.5 µm.

The width of the reaction-diffusion conduit can be from about 0.1 µm to about 1 mm. The width of the reaction-diffusion conduit can be from about 0.1 µm to about 750 µm. The width of the reaction-diffusion conduit can be from about 0.1 µm to about 500 µm. The width of the reaction-diffusion conduit can be from about 0.1 µm to about 250 µm. The width of the reaction-diffusion conduit can be from about 0.1 µm to about 100 µm. The width of the reaction-diffusion conduit can be from about 0.1 µm to about 50 µm. The width of the reaction-diffusion conduit can be from about 0.1 µm to about 25 µm. The width of the reaction-diffusion conduit can be from about 0.1 µm to about 10 µm. The width of the reaction-diffusion conduit can be from about 0.1 µm to about 5 µm. The width of the reaction-diffusion conduit can be from about 0.1 µm to about 1 µm. The width of the reaction-diffusion conduit can be from about 0.1 µm to about 0.5 µm.

The width of the reaction-diffusion conduit can be about 1 mm. The width of the reaction-diffusion conduit can be about 750 µm. The width of the reaction-diffusion conduit can be about 500 µm. The width of the reaction-diffusion conduit can be about 250 µm. The width of the reaction-diffusion conduit can be about 100 µm. The width of the reaction-diffusion conduit can be about 50 µm. The width of the reaction-diffusion conduit can be about 25 µm. The width of the reaction-diffusion conduit can be about 10 µm. The width of the reaction-diffusion conduit can be about 5 µm. The width of the reaction-diffusion conduit can be about 1 µm. The width of the reaction-diffusion conduit can be about 0.5 µm.

The cross-section of the reaction-diffusion conduit may be, for example, a rectangle, a square, a circle, a semi-circle, a triangle, a trapezoid. The reaction-diffusion conduit may be, for example, straight, curved, spiral, or contain turns.

In some embodiments, the device can have one reaction-diffusion conduct in fluid communication with the sample chamber. In other embodiments, the device can have a plurality of reaction-diffusion conduits in fluid communication with the sample chamber. For example, the device can have between 2 to about 100 reaction-diffusion conduits in fluid communication with the sample chamber. In some aspects, the device can have 2 reaction-diffusion conduits in fluid communication with the sample chamber. In some aspects, the device can have 3 reaction-diffusion conduits in fluid communication with the sample chamber. In some aspects the device can have 4 reaction-diffusion conduits in fluid communication with the sample chamber. In some aspects the device can have 5 reaction-diffusion conduits in fluid communication with the sample chamber. In some aspects, the device can have 10 reaction-diffusion conduits in fluid communication with the sample chamber. In some aspects the device can have 15 reaction-diffusion conduits in fluid communication with the sample chamber. In some aspects the device can have 20 reaction-diffusion conduits in fluid communication with the sample chamber. In some aspects, the device can have more than 20 reaction-diffusion conduits in fluid communication with the sample chamber.

In some embodiments, the device can have 1 sample chamber, said sample chamber having at least one reaction-diffusion conduit in fluid communication therewith. In some aspects, the device can have 1 sample chamber, said sample chamber having 1 reaction-diffusion conduit in fluid communication therewith. In some aspects, the device can have 1 sample chamber, said sample chamber having a plurality of reaction-diffusion conduits in fluid communication therewith. For example, in some aspects, the device can have 1 sample chamber, said sample chamber having about 2 to about 100 reaction-diffusion conduits in fluid communication therewith.

In other embodiments, the device can have a plurality of sample chambers, each sample chamber having at least one reaction-diffusion conduit in fluid communication therewith. For example, the device can have 1 to 100 sample chambers, each sample chamber having at least one reaction-diffusion conduit in fluid communication therewith. In some aspects, the device can have 1 sample chambers, each sample chamber having 2-100 reaction-diffusion conduits in fluid communication therewith. In some aspects, the device can have 2 sample chambers, each sample chamber having 2-100 reaction-diffusion conduits in fluid communication therewith. In some aspects, the device can have 3 sample chambers, each sample chamber having 2-100 reaction-diffusion conduits in fluid communication therewith. In some aspects, the device can have 4 sample chambers, each sample chamber having 2-100 reaction-diffusion conduits in fluid communication therewith. In some aspects, the device can have 5 sample chambers, each sample chamber having 2-100 reaction-diffusion conduits in fluid communication therewith. In some aspects, the device can have 10 sample chambers, each sample chamber having 2-100 reaction-diffusion conduits in fluid communication therewith. In some aspects, the device can have 50 sample chambers, each sample chamber having 2-100 reaction-diffusion conduits in fluid communication therewith. In some aspects, the device can have 75 sample chambers, each sample chamber having 2-100 reaction-diffusion conduits in fluid communication therewith. In some aspects, the device can have 100 sample chambers, each sample chamber having 2-100 reaction-diffusion conduits in fluid communication therewith.

In some embodiments, the device can have a plurality of sample chambers, wherein at least some of the sample chambers have a plurality of reaction-diffusion conduits in fluid communication therewith. Thus, in some aspects, 100% of said plurality of sample chambers have a plurality of reaction-diffusion conduits in fluid communication therewith. In some aspects, less than 100% of said plurality of sample chambers have a plurality of reaction-diffusion conduits in fluid communication therewith. In some aspects, 90% of said plurality of sample chambers have a plurality of reaction-diffusion conduits in fluid communication therewith. In some aspects, 80% of said plurality of sample chambers have a plurality of reaction-diffusion conduits in fluid communication therewith. In some aspects, 70% of said plurality of sample chambers have a plurality of reaction-diffusion conduits in fluid communication therewith. In some aspects, 60% of said plurality of sample chambers have a plurality of reaction-diffusion conduits in fluid communication therewith. In some aspects, 50% of said plurality of sample chambers have a plurality of reaction-diffusion conduits in fluid communication therewith. In some aspects, 40% of said plurality of sample chambers have a plurality of reaction-diffusion conduits in fluid communication therewith. In some aspects, 30% of said plurality of sample chambers have a plurality of reaction-diffusion conduits in fluid communication therewith. In some aspects, 20% of said plurality of sample chambers have a plurality of reaction-diffusion conduits in fluid communication therewith. In some aspects, 10% of said plurality of sample chambers have a plurality of reaction-diffusion conduits in fluid communication therewith. In some aspects, 5% of said plurality of sample chambers have a plurality of reaction-diffusion conduits in fluid communication therewith. In some aspects, 1% of said plurality of sample chambers have a plurality of reaction-diffusion conduits in fluid communication therewith.

In some aspects, about 1% to about 100% of said plurality of sample chambers have a plurality of reaction-diffusion conduits in fluid communication therewith. In some aspects, about 5% to about 100% of said plurality of sample chambers have a plurality of reaction-diffusion conduits in fluid communication therewith. In some aspects, about 10% to about 100% of said plurality of sample chambers have a plurality of reaction-diffusion conduits in fluid communication therewith. In some aspects, about 15% to about 100% of said plurality of sample chambers have a plurality of reaction-diffusion conduits in fluid communication therewith. In some aspects, about 25% to about 100% of said plurality of sample chambers have a plurality of reaction-diffusion conduits in fluid communication therewith. In some aspects, about 40% to about 100% of said plurality of sample chambers have a plurality of reaction-diffusion conduits in fluid communication therewith. In some aspects, about 55% to about 100% of said plurality of sample chambers have a plurality of reaction-diffusion conduits in fluid communication therewith. In some aspects, about 70% to about 100% of said plurality of sample chambers have a plurality of reaction-diffusion conduits in fluid communication therewith. In some aspects, about 85% to about 100% of said plurality of sample chambers have a plurality of reaction-diffusion conduits in fluid communication therewith. In some aspects, about 1% to about 90% of said plurality of sample chambers have a plurality of reaction-diffusion conduits in fluid communication therewith. In some aspects, about 1% to about 80% of said plurality of sample chambers have a plurality of reaction-diffusion conduits in fluid communication therewith. In some aspects, about 1% to about 70% of said plurality of sample chambers have a plurality of reaction-diffusion conduits in fluid communication therewith. In some aspects, about 1% to about 60% of said plurality of sample chambers have a plurality of reaction-diffusion conduits in fluid communication therewith. In some aspects, about 1% to about 50% of said plurality of sample chambers have a plurality of reaction-diffusion conduits in fluid communication therewith. In some aspects, about 1% to about 40% of said plurality of sample chambers have a plurality of reaction-diffusion conduits in fluid communication therewith. In some aspects, about 1% to about 30% of said plurality of sample chambers have a plurality of reaction-diffusion conduits in fluid communication therewith. In some aspects, about 1% to about 20% of said plurality of sample chambers have a plurality of reaction-diffusion conduits in fluid communication therewith. In some aspects, about 1% to about 10% of said plurality of sample chambers have a plurality of reaction-diffusion conduits in fluid communication therewith.

The device can have at least one sample chamber having a known quantity of a preselected, nucleic acid molecule, which can serve has a "positive control" or "calibration" nuclemeter.

The disclosed devices can be used in combination with porous membranes for nucleic acid extraction, concentration, and purification. Suitable porous membranes include, but are not limited to, silica membrane, Whatman FTA membrane, alumina membrane, cellulose membrane. Such porous membranes specifically bind nucleic acids allowing other non-nucleic acid material to pass through the membrane. For example, in some embodiments, a nucleic acid sample can be incubated with a porous membrane, the porous membrane can be washed to remove non-nucleic acid material, and the porous membrane can be added to the sample chamber. In other embodiments, the device can have a sample chamber having a porous membrane for nucleic acids extraction, concentration, and purification. Suitable sample chambers include those disclosed in U.S. application Ser. No. 14/001,347 (US2014/0162244). In some aspects, the porous membrane can be removably located within the sample chamber. In some aspects, the porous membrane can be attached to the inside of the sample chamber. In other aspects, all or a portion of the sample chamber can be made from a porous membrane.

The sample chamber and/or the reaction-diffusion conduit can be made of a porous polymer or cellulose material. The blend of reactants can be stored in the porous polymer or cellulose material until the device is ready for use.

In some embodiments, the device further comprises a waste conduit. The waste conduit can, for example, be used to empty the sample chamber, decrease the volume of the sample in the sample chamber, extract amplified material from the sample chamber, remove non-nucleic acid material from the sample chamber, or any combination thereof.

The waste conduit and reaction-diffusion conduits can have a valve to open and close the conduit, allowing and preventing, respectively, sample from flowing into the conduit. For example, in some embodiments, the sample chamber contains a porous membrane. To extract, concentrate, and/or purify the nucleic acid sample, the valves on both the waste conduit and reaction-diffusion conduits can be closed to allow the sample to interact with the membrane. To remove non-nucleic acid material, the valve on the waste conduit can be opened, while the valve on the reaction-diffusion conduit can remain closed. After the waste is removed, the valve on the waste conduit can be closed. Prior to amplification, the appropriate reactant mixture can be added to the sample chamber and the valve on the reaction-diffusion conduit can be opened, allowing diffusion of the amplified sample into the reaction-diffusion conduit. In some embodiments, the valve can be a passive valve. In other embodiments, the valve can be an active valve.

In some embodiments the device further comprises a light source. Suitable light sources include, but are not limited to, light-emitting diode (LED), compact fluorescent lamp (CFL), or incandescent.

The device can further comprise an optical imager. Suitable optical imagers include, but are not limited to, a fluorescent microscope or a camera. In some aspects, the camera can be from a cellular telephone, smart-phone camera, tablet computer, or computer.

The device can be operatively connected to a controller or computer.

In some embodiments, the device further comprises a ruler along the length of the reaction-diffusion conduit.

The device can further comprise a heat source. Suitable heat sources include a thermoelectric unit, an electric heater, an exothermic reactor, a laser, or any combination thereof. In some aspects, the heat source can provide a spatially varying temperature distribution along the length of the reaction-diffusion conduit. Such a heat source enables different temperatures to be applied to different regions of the reaction-diffusion conduit at different times. The temperature can be regulated with a phase change material. In some embodiments, the temperature gradient along the reaction-diffusion conduit can be linear. The temperature in the sample chamber can be different from the temperature in the reaction-diffusion conduit. In other embodiments, the temperature in the sample chamber can be the same as the temperature in the reaction-diffusion conduit.

In some embodiments, each of the chamber and the at least one reaction-diffusion conduit hold a blend of reactants for nucleic acid amplification. In other embodiments, each of the chamber and the at least on reaction-diffusion conduit are capable of holding a blend of reactants for nucleic acid amplification. The blend of reactants can comprise a plurality of primers and enzymes. In some embodiments, the blend of reactants can further comprise one or more types of reporters. Those skilled in the art would understand that numerous primers, enzymes, and reporters are suitable for nucleic acid amplification procedures. Primers of any length suitable for nucleic acid amplification can be used herein. One skilled in the art would know that primers of nucleic acid amplification are used in pairs—a forward or sense primer and a reverse or antisense primer. "Plurality of primers" and "primer sets" are used interchangeably herein and refer to at least one pair of primers. In some embodiments, the plurality of primers can be a pair of primers. In some embodiments, the plurality of primers can be 2 pairs of primers. In some embodiments, plurality of primers can be more than 2 pairs of primers. Enzymes suitable for nucleic acid amplification include, but are not limited to, DNA polymerase, RNA-dependent DNA polymerase (reverse transcriptase), or DNA-dependent RNA polymerase (RNA polymerase). As used herein, the term "reporter" means any tag, label, or dye that can bind to, or intercalate within, the nucleic acid molecule or be activated by byproducts of the amplification process to enable visualization of the nucleic acid molecule or the amplification process. Suitable reporters include, but are not limited to, fluorescent labels/tags/dyes, intercalating agents, molecular beacon labels, and bioluminescent molecules. The sample chamber and reaction-diffusion conduit may contain a mixture of primers engineered to be specific to various targets, enabling the concurrent amplification and detection of multiple targets. The sample chamber may contain universal primers to amplify all targets, while the the reaction-diffusion conduits may contain primers for specific targets. In some embodiments, the universal primers in the sample chamber can be immobilized to prevent passage of the primers into the reaction-diffusion conduit. Primers can be immobilized to, for example, the sample chamber or something within the sample chamber that cannot pass into the reaction-diffusion conduit. The reaction-diffusion conduit may also contain reporters (molecular beacons) each engineered to bind to a specific target and each emitting at different range of the spectrum, allowing the detector, with appropriate filters, to image each target separately.

Other reactants include, but are not limited to, buffers and dNTPs.

The blend of reactants, or a portion thereof, can be pre-stored in the device. In some embodiments, the blend of reactants, or a portion thereof, are pre-stored in the device and are released upon an increase in temperature. For example, the blend of reactants can be released when the device is heated to its operating temperature.

The blend of reactants can be liquid or can be in a form that is capable of forming a liquid upon a change in temperature, such as a gel or solid. For example, the blend of reactants can be encased in, embedded in, or surrounded by, a material that melts with increasing temperatures, such as, for example, paraffin. In yet other embodiments, the primers and/or enzymes may be immobilized to the conduit walls or to a porous matrix that fills the reaction-diffusion conduit.

In some embodiments, the device can have at least two nuclemeters, each containing different primers. The primers can recognize the same nucleic acid molecule but differ in length. Alternatively, the primers can recognize different nucleic acid molecules and be the same length. Alternatively, the primers can recognize different nucleic acid molecules and be different lengths.

A single nuclemeter can have multiple reaction-diffusion conduits, at least two of said reaction-diffusion conduits containing different primers. For example, one reaction-diffusion conduit can contain a first plurality of primers and another reaction-diffusion conduit can contain a second plurality of primers, the second plurality of primers being different from the first plurality of primers. In such a device, the sample chamber can contain: a mix of a first plurality of primers and second plurality of primers; only a first plurality of primers; only a second plurality of primers; or a third plurality of primers.

In some embodiments, the blend of reactants in the sample chamber and the blend of reactants in the conduit are capable of amplifying different nucleic acid molecules. In some aspects, for example, the blend of reactants in the sample chamber and the blend of reactants in the conduit are capable of amplifying at least two different nucleic acid molecules.

In some embodiments, at least one of the reaction-diffusion conduits can contain at least one polymer. In some embodiments, at least one of the reaction-diffusion conduit and the sample chamber can contain at least one polymer. The presence of the polymer in the reaction-diffusion conduit or reaction-diffusion conduit and sample chamber can slow the diffusion of the amplified DNA and control the speed of propagation of the reaction front in the reaction-diffusion conduit, so that the diffusion may be easily monitored and/or quantified. In some embodiments, the at least one polymer can be a gel. In embodiments wherein the at least one polymer is a gel, the primers, enzymes, or both can be immobilized to the gel. In some embodiments, the polymer is a solid at an ambient temperature and a liquid at an amplification temperature. As used herein, "ambient temperature" refers to the temperature of the device prior to the amplification procedure. Thus, prior to the amplification procedure, the polymer can be a solid. As the temperature increases at the start of or during the amplification procedure, the polymer can turn into a liquid. In other embodiment, the reaction-diffusion conduit contains gel.

The disclosed devices can be used for a number of purposes including, but not limited to, melting curve analysis, reverse transcription, identifying a nucleic acid in a sample, diagnosis, quantifying the number of nucleic acid molecules in a sample, and testing amplification reactants. In some embodiments, the sample chamber, reaction-diffusion conduit, or both are suitable for reverse transcription.

Nucleic ACID AMPLIFICATION MONITORS

Also disclosed herein are nucleic acid amplification monitors comprising a substrate and, on or forming a part of the substrate, and a plurality of nuclemeters. Each nuclemeter comprises an sample chamber and at least one reaction-diffusion conduit in fluid communication with the chamber. In some embodiments, each of the chamber and the at least on reaction-diffusion conduit hold a blend of reactants for nucleic acid amplification. In other embodiments, each of the chamber and the at least one reaction-diffusion conduit are capable of holding a blend of reactants for nucleic acid amplification.

Suitable substrates include, but are not limited to, glass, plastic, polymers, metal, silicon, aluminum oxide membrane, acrylic, paper, or any combination thereof. In some embodiments the substrate is a polymeric chip. Polymeric chips can be composed of numerous polymers including, but not limited to, polycarbonate (PC), poly-methyl methacrylate (PMMA), cyclic olefin co-polymers (COC), or any combination thereof. In one embodiment, the polymeric chip comprises polymethyl methacrylate (PMMA).

In some embodiments, the plurality of nuclemeters can be on the substrate. For example, the nuclemeter and the substrate can be separate components, and can be combined or attached such that the nuclemeter is on a top surface of the substrate. In other aspects, the nuclemeter and substrate can be from a single component wherein the nuclemeter is located on a top surface of the substrate. In other embodiments, the nuclemeter can form a part of the substrate. For example, the nuclemeter can be etched into the substrate. In other embodiments, the substrate can be molded to form the nuclemeter.

The sample chamber can have a size and shape suitable for containing a nucleic acid amplification reaction. For example, the cross-section of the sample chamber can have a variety of suitable shapes, including, but not limited to, square, rectangular, triangular, pentagonal, hexagonal, heptagonal, octagonal, nonagonal, decagonal, round, or elliptical.

The bottom of the sample chamber can be flat, substantially flat, conical, round, substantially round, or pointed.

The sample chamber can be a droplet covered by oil, wherein the droplet is propelled by means such as electrowetting to make hydraulic connection with the reaction-diffusion conduit.

The sample chamber and diffusion-reaction conduit can be separated with a barrier. The barrier can be configured to block passage of reactants between the sample chamber and the reaction-diffusion conduit during sample introduction, nucleic acid isolation, etc. and can be configured to allow passage of reactants between the sample chamber and the reaction-diffusion conduit at a specified time or in response to an event. In some embodiments, the barrier can be removable. In some aspects, for example, the barrier can be physically removed from the nuclemeter. In some embodiments, the barrier can be degradable. For example, the barrier can be composed of, or can comprise, a material that degrades. In some embodiments, the barrier can be dissolvable. For example, the barrier can be composed of a material that dissolves in solution. Exemplary materials that dissolve in solution include, for example, salt. In some embodiments, the barrier can be capable of being melted. For example, the barrier can be composed of, or can comprise, a phase change material that melts at a certain temperature. In some embodiments, the barrier can be movable. For example, the barrier can be configured to open or otherwise allow passage of sample between the sample chamber and the reaction diffusion conduit in response to a force, such as the amplification of the nucleic acid molecule or other surface tension.

The barrier can allow for a two-step or nested-like amplification. For example, two different amplification reactions can be run; one in the sample chamber and one in the reaction-diffusion conduit. The reaction in the sample chamber can, for example, amplify nucleic acid molecules non-specifically. Once the reaction in the sample chamber is complete, the barrier can be removed, dissolved, degraded, melted, etc. allowing the amplified nucleic acid molecules to diffuse into the reaction-diffusion conduit, which can contain primers for a specific nucleic acid molecule. Within the reaction-diffusion conduit, specific nucleic acid molecules will then be amplified. The two reactions can operate with different enzymes, temperatures, etc.

The sample chamber has a size suitable for a containing a nucleic acid amplification reaction. Suitable sizes include sample chambers having a volume of from about 0.1 µl to about 300 µl. In one embodiment, the sample chamber has a volume of about 0.1 µl. In one embodiment, the sample chamber has a volume of about 0.5 µl. In one embodiment, the sample chamber has a volume of about 1 µl. In one embodiment, the sample chamber has a volume of about 10 µl. In one embodiment, the sample chamber has a volume of about 20 µl. In one embodiment, the sample chamber has a volume of about 50 µl. In one embodiment, the sample chamber has a volume of about 100 µl. In one embodiment, the sample chamber has a volume of about 150 µl. In one embodiment, the sample chamber has a volume of about 200 µl. In one embodiment, the sample chamber has a volume of about 250 µl. In one embodiment, the sample chamber has a volume of about 300 µl. In some embodiments, the sample chamber has a volume greater than 300 µl.

The sample chamber can be from about 0.1 µl to about 300 µl in volume. In some aspects, the sample chamber can be from about 0.1 µl to about 250 µl in volume. The sample chamber can be from about 0.1 µl to about 200 µl in volume. The sample chamber can be from about 0.1 µl to about 150 µl in volume. The sample chamber can be from about 0.1 µl to about 100 µl in volume. The sample chamber can be from about 0.1 µl to about 50 µl in volume. The sample chamber can be from about 10 µl to about 300 µl in volume. The sample chamber can be from about 10 µl to about 200 µl in volume. The sample chamber can be from about 10 µl to about 150 µl in volume. The sample chamber can be from about 10 µl to about 100 µl in volume. The sample chamber can be from about 10 µl to about 50 µl in volume. In some aspects, the sample chamber can be from about 25 µl to about 300 µl in volume. The sample chamber can be from about 50 µl to about 300 µl in volume. The sample chamber can be from about 75 µl to about 300 µl in volume. The sample chamber can be from about 100 µl to about 300 µl in volume. The sample chamber can be from about 125 µl to about 300 µl in volume. The sample chamber can be from about 150 µl to about 300 µl in volume. The sample chamber can be from about 175 µl to about 300 µl in volume. The sample chamber can be from about 200 µl to about 300 µl in volume. The sample chamber can be from about 225 µl to about 300 µl in volume. The sample chamber can be from about 250 µl to about 300 µl in volume. The sample chamber can be from about 275 µl to about 300 µl in volume.

The height of the sample chamber can be from about 0.05 mm to about 10 mm. The height of the sample chamber can be from about 0.1 mm to about 9 mm. The height of the sample chamber can be from about 0.2 mm to about 8 mm. The height of the sample chamber can be from about 0.3 mm to about 7 mm. The height of the sample chamber can be from about 0.4 mm to about 6 mm. The height of the sample chamber can be from about 0.5 mm to about 5 mm. The height of the sample chamber can be from about 0.6 mm to about 4 mm. The height of the sample chamber can be from about 0.7 mm to about 3 mm. The height of the sample chamber can be from about 0.8 mm to about 2 mm. The height of the sample chamber can be from about 0.9 mm to about 1 mm.

In some aspects, the height of the sample chamber can be about 0.05 mm. In some aspects, the height of the sample chamber can be about 0.1 mm. In some aspects, the height of the sample chamber can be about 0.2 mm. In some aspects, the height of the sample chamber can be about 0.3 mm. In some aspects, the height of the sample chamber can be about 0.4 mm. In some aspects, the height of the sample chamber can be about 0.5 mm. In some aspects, the height of the sample chamber can be about 0.6 mm. In some aspects, the height of the sample chamber can be about 0.7 mm. In some aspects, the height of the sample chamber can be about 0.8 mm. In some aspects, the height of the sample chamber can be about 0.9 mm. In some aspects, the height of the sample chamber can be about 1 mm. In some aspects, the height of the sample chamber can be about 2.5 mm. In some aspects, the height of the sample chamber can be about 5 mm. In some aspects, the height of the sample chamber can be about 7.5 mm. In some aspects, the height of the sample chamber can be about 10 mm.

The width of the sample chamber can be from about 0.05 mm to about 5 mm. The width of the sample chamber can be from about 0.1 mm to about 4 mm. The width of the sample chamber can be from about 0.2 mm to about 3 mm. The width of the sample chamber can be from about 0.3 mm to about 2 mm. The width of the sample chamber can be from about 0.4 mm to about 1 mm. The width of the sample chamber can be from about 0.5 mm to about 0.9 mm. The width of the sample chamber can be from about 0.6 mm to about 0.8 mm.

The width of the sample chamber can be about 0.05. The width of the sample chamber can be about 0.1 mm. The width of the sample chamber can be about 0.2 mm. The width of the sample chamber can be about 0.3 mm. The width of the sample chamber can be about 0.4 mm. The width of the sample chamber can be about 0.5 mm. The width of the sample chamber can be from 0.6 mm. The width of the sample chamber can be about 0.7. The width of the sample chamber can be about 0.8 mm. The width of the sample chamber can be about 0.9 mm. The width of the sample chamber can be about 1 mm. The width of the sample chamber can be about 2 mm. The width of the sample chamber can be about 3 mm. The width of the sample chamber can be about 4 mm. The width of the sample chamber can be about 2 mm. The width of the sample chamber can be about 5 mm.

The length of the reaction-diffusion conduit can be from about 0.05 mm to about 100 mm. The length of the reaction-diffusion conduit can be from about 0.05 mm to about 75 mm. The length of the reaction-diffusion conduit can be from about 0.05 mm to about 50 mm. The length of the reaction-diffusion conduit can be from about 0.05 mm to about 25 mm. The length of the reaction-diffusion conduit can be from about 0.05 mm to about 10 mm. The length of the reaction-diffusion conduit can be from about 0.05 mm to about 5 mm. The length of the reaction-diffusion conduit can be from about 0.05 mm to about 2.5 mm. The length of the reaction-diffusion conduit can be from about 0.05 mm to about 1 mm. The length of the reaction-diffusion conduit can be from about 0.05 mm to about 0.5 mm.

The length of the reaction-diffusion conduit can be about 100 mm. The length of the reaction-diffusion conduit can be about 75 mm. The length of the reaction-diffusion conduit can be about 50 mm. The length of the reaction-diffusion conduit can be about 25 mm. The length of the reaction-diffusion conduit can be about 10 mm. The length of the reaction-diffusion conduit can be about 5 mm. The length of the reaction-diffusion conduit can be about 2.5 mm. The length of the reaction-diffusion conduit can be about 1 mm. The length of the reaction-diffusion conduit can be about 0.5 mm.

The height of the reaction-diffusion conduit can be from about 0.1 µm to about 1 mm. The height of the reaction-diffusion conduit can be from about 0.1 µm to about 750 µm. The height of the reaction-diffusion conduit can be from about 0.1 µm to about 500 µm. The height of the reaction-diffusion conduit can be from about 0.1 µm to about 250 µm. The height of the reaction-diffusion conduit can be from about 0.1 µm to about 100 µm. The height of the reaction-diffusion conduit can be from about 0.1 µm to about 50 µm. The height of the reaction-diffusion conduit can be from about 0.1 µm to about 25 µm. The height of the reaction-diffusion conduit can be from about 0.1 µm to about 10 µm. The height of the reaction-diffusion conduit can be from about 0.1 µm to about 5 µm. The height of the reaction-diffusion conduit can be from about 0.1 µm to about 1 µm. The height of the reaction-diffusion conduit can be from about 0.1 µm to about 0.5 µm.

The height of the reaction-diffusion conduit can be about 1 mm. The height of the reaction-diffusion conduit can be about 750 µm. The height of the reaction-diffusion conduit can be about 500 µm. The height of the reaction-diffusion conduit can be about 250 µm. The height of the reaction-diffusion conduit can be about 100 µm. The height of the reaction-diffusion conduit can be about 50 µm. The height of the reaction-diffusion conduit can be about 25 µm. The height of the reaction-diffusion conduit can be about 10 µm. The height of the reaction-diffusion conduit can be about 5 µm. The height of the reaction-diffusion conduit can be about 1 µm. The height of the reaction-diffusion conduit can be about 0.5 µm.

The width of the reaction-diffusion conduit can be from about 0.1 µm to about 1 mm. The width of the reaction-diffusion conduit can be from about 0.1 µm to about 750 µm. The width of the reaction-diffusion conduit can be from about 0.1 µm to about 500 µm. The width of the reaction-diffusion conduit can be from about 0.1 µm to about 250 µm. The width of the reaction-diffusion conduit can be from about 0.1 µm to about 100 µm. The width of the reaction-diffusion conduit can be from about 0.1 µm to about 50 µm. The width of the reaction-diffusion conduit can be from about 0.1 µm to about 25 µm. The width of the reaction-diffusion conduit can be from about 0.1 µm to about 10 µm. The width of the reaction-diffusion conduit can be from about 0.1 µm to about 5 µm. The width of the reaction-diffusion conduit can be from about 0.1 µm to about 1 µm. The width of the reaction-diffusion conduit can be from about 0.1 µm to about 0.5 µm.

The width of the reaction-diffusion conduit can be about 1 mm. The width of the reaction-diffusion conduit can be about 750 µm. The width of the reaction-diffusion conduit can be about 500 µm. The width of the reaction-diffusion conduit can be about 250 µm. The width of the reaction-diffusion conduit can be about 100 µm. The width of the reaction-diffusion conduit can be about 50 µm. The width of the reaction-diffusion conduit can be about 25 µm. The width of the reaction-diffusion conduit can be about 10 µm. The width of the reaction-diffusion conduit can be about 5 µm. The width of the reaction-diffusion conduit can be about 1 µm. The width of the reaction-diffusion conduit can be about 0.5 µm.

The cross-section of the reaction-diffusion conduit may be, for example, a rectangle, a square, a circle, a semi-circle, a triangle, a trapezoid. The reaction-diffusion conduit may be, for example, straight, curved, spiral, or contain turns.

In some embodiments, the nucleic acid amplification monitor can have 1 reaction-diffusion conduct in fluid communication with the sample chamber. In other embodiments, the nucleic acid amplification monitor can have a plurality of reaction-diffusion conduits in fluid communication with the sample chamber. For example, the nucleic acid amplification monitor can have between 2 to about 100 reaction-diffusion conduits in fluid communication with the sample chamber. In some aspects, the nucleic acid amplification monitor can have 2 reaction-diffusion conduits in fluid communication with the sample chamber. In some aspects, the nucleic acid amplification monitor can have 3 reaction-diffusion conduits in fluid communication with the sample chamber. In some aspects the nucleic acid amplification monitor can have 4 reaction-diffusion conduits in fluid communication with the sample chamber. In some aspects the nucleic acid amplification monitor can have 5 reaction-diffusion conduits in fluid communication with the sample chamber. In some aspects, the nucleic acid amplification monitor can have 10 reaction-diffusion conduits in fluid communication with the sample chamber. In some aspects the nucleic acid amplification monitor can have 15 reaction-diffusion conduits in fluid communication with the sample chamber. In some aspects the nucleic acid amplification monitor can have 20 reaction-diffusion conduits in fluid communication with the sample chamber. In some aspects, the nucleic acid amplification monitor can have more than 20 reaction-diffusion conduits in fluid communication with the sample chamber.

In some embodiments, the nucleic acid amplification monitor can have 1 sample chamber, said sample chamber having at least one reaction-diffusion conduit in fluid communication therewith. In some aspects, the nucleic acid amplification monitor can have 1 sample chamber, said sample chamber having 1 reaction-diffusion conduit in fluid communication therewith. In some aspects, the nucleic acid amplification monitor can have 1 sample chamber, said sample chamber having a plurality of reaction-diffusion conduits in fluid communication therewith. For example, in some aspects, the nucleic acid amplification monitor can have 1 sample chamber, said sample chamber having about 2 to about 100 reaction-diffusion conduits in fluid communication therewith.

In other embodiments, the nucleic acid amplification monitor can have a plurality of sample chambers, each sample chamber having at least one reaction-diffusion conduit in fluid communication therewith. For example, the nucleic acid amplification monitor can have 1 to 100 sample chambers, each sample chamber having at least one reaction-diffusion conduit in fluid communication therewith. In some aspects, the nucleic acid amplification monitor can have 1 sample chambers, each sample chamber having 2-100 reaction-diffusion conduits in fluid communication therewith. In some aspects, the nucleic acid amplification monitor can have 2 sample chambers, each sample chamber having 2-100 reaction-diffusion conduits in fluid communication therewith. In some aspects, the nucleic acid amplification monitor can have 3 sample chambers, each sample chamber having 2-100 reaction-diffusion conduits in fluid communication therewith. In some aspects, the nucleic acid amplification monitor can have 4 sample chambers, each sample chamber having 2-100 reaction-diffusion conduits in fluid communication therewith. In some aspects, the nucleic acid amplification monitor can have 5 sample chambers, each sample chamber having 2-100 reaction-diffusion conduits in fluid communication therewith. In some aspects, the nucleic acid amplification monitor can have 10 sample chambers, each sample chamber having 2-100 reaction-diffusion conduits in fluid communication therewith. In some aspects, the nucleic acid amplification monitor can have 50 sample chambers, each sample chamber having 2-100 reaction-diffusion conduits in fluid communication therewith. In some aspects, the nucleic acid amplification monitor can have 75 sample chambers, each sample chamber having 2-100 reaction-diffusion conduits in fluid communication therewith. In some aspects, the nucleic acid amplification monitor can have 100 sample chambers, each sample chamber having 2-100 reaction-diffusion conduits in fluid communication therewith.

In some embodiments, the nucleic acid amplification monitor can have a plurality of sample chambers, wherein at least some of the sample chambers have a plurality of reaction-diffusion conduits in fluid communication therewith. Thus, in some aspects, 100% of said plurality of sample chambers have a plurality of reaction-diffusion conduits in fluid communication therewith. In some aspects, less than 100% of said plurality of sample chambers have a plurality of reaction-diffusion conduits in fluid communication therewith. In some aspects, 90% of said plurality of sample chambers have a plurality of reaction-diffusion conduits in fluid communication therewith. In some aspects, 80% of said plurality of sample chambers have a plurality of reaction-diffusion conduits in fluid communication therewith. In some aspects, 70% of said plurality of sample chambers have a plurality of reaction-diffusion conduits in fluid communication therewith. In some aspects, 60% of said plurality of sample chambers have a plurality of reaction-diffusion conduits in fluid communication therewith. In some aspects, 50% of said plurality of sample chambers have a plurality of reaction-diffusion conduits in fluid communication therewith. In some aspects, 40% of said plurality of sample chambers have a plurality of reaction-diffusion conduits in fluid communication therewith. In some aspects, 30% of said plurality of sample chambers have a plurality of reaction-diffusion conduits in fluid communication therewith. In some aspects, 20% of said plurality of sample chambers have a plurality of reaction-diffusion conduits in fluid communication therewith. In some aspects, 10% of said plurality of sample chambers have a plurality of reaction-diffusion conduits in fluid communication therewith. In some aspects, 5% of said plurality of sample chambers have a plurality of reaction-diffusion conduits in fluid communication therewith. In some aspects, 1% of said plurality of sample chambers have a plurality of reaction-diffusion conduits in fluid communication therewith.

In some aspects, about 1% to about 100% of said plurality of sample chambers have a plurality of reaction-diffusion conduits in fluid communication therewith. In some aspects, about 5% to about 100% of said plurality of sample chambers have a plurality of reaction-diffusion conduits in fluid communication therewith. In some aspects, about 10% to about 100% of said plurality of sample chambers have a plurality of reaction-diffusion conduits in fluid communication therewith. In some aspects, about 15% to about 100% of said plurality of sample chambers have a plurality of reaction-diffusion conduits in fluid communication therewith. In some aspects, about 25% to about 100% of said plurality of sample chambers have a plurality of reaction-diffusion conduits in fluid communication therewith. In some aspects, about 40% to about 100% of said plurality of sample chambers have a plurality of reaction-diffusion conduits in fluid communication therewith. In some aspects, about 55% to about 100% of said plurality of sample chambers have a plurality of reaction-diffusion conduits in fluid communication therewith. In some aspects, about 70% to about 100% of said plurality of sample chambers have a plurality of reaction-diffusion conduits in fluid communication therewith. In some aspects, about 85% to about 100% of said plurality of sample chambers have a plurality of reaction-diffusion conduits in fluid communication therewith. In some aspects, about 1% to about 90% of said plurality of sample chambers have a plurality of reaction-diffusion conduits in fluid communication therewith. In some aspects, about 1% to about 80% of said plurality of sample chambers have a plurality of reaction-diffusion conduits in fluid communication therewith. In some aspects, about 1% to about 70% of said plurality of sample chambers have a plurality of reaction-diffusion conduits in fluid communication therewith. In some aspects, about 1% to about 60% of said plurality of sample chambers have a plurality of reaction-diffusion conduits in fluid communication therewith. In some aspects, about 1% to about 50% of said plurality of sample chambers have a plurality of reaction-diffusion conduits in fluid communication therewith. In some aspects, about 1% to about 40% of said plurality of sample chambers have a plurality of reaction-diffusion conduits in fluid communication therewith. In some aspects, about 1% to about 30% of said plurality of sample chambers have a plurality of reaction-diffusion conduits in fluid communication therewith. In some aspects, about 1% to about 20% of said plurality of sample chambers have a plurality of reaction-diffusion conduits in fluid communication therewith. In some aspects, about 1% to about 10% of said plurality of sample chambers have a plurality of reaction-diffusion conduits in fluid communication therewith.

The nucleic acid amplification monitor can have at least one sample chamber having a known quantity of a preselected, nucleic acid molecule, which can serve has a "positive control" or "calibration" nuclemeter.

The disclosed nucleic acid amplification monitors can be used in combination with porous membranes for nucleic acid extraction, concentration, and purification. Suitable porous membranes include, but are not limited to, silica membrane, Whatman FTA membrane, alumina membrane, cellulose membrane. Such porous membranes specifically bind nucleic acids allowing other non-nucleic acid material to pass through the membrane. For example, in some embodiments, a nucleic acid sample can be incubated with a porous membrane, the porous membrane can be washed to remove non-nucleic acid material, and the porous membrane can be added to the sample chamber. In other embodiments, the nucleic acid amplification monitor can have an sample chamber having a porous membrane for nucleic acids extraction, concentration, and purification. Suitable sample chambers include those disclosed in U.S. application Ser. No. 14/001,347 (US2014/0162244). In some aspects, the porous membrane can be removably located within the sample chamber. In some aspects, the porous membrane can be attached to the inside of the sample chamber. In other aspects, all or a portion of the sample chamber can be made from a porous membrane.

In some embodiments, the nucleic acid amplification monitor further comprises a waste conduit. The waste conduit can, for example, be used to empty the sample chamber, decrease the volume of the sample in the sample chamber, extract amplified material from the sample chamber, remove non-nucleic acid material from the sample chamber, or any combination thereof.

The waste conduit and reaction-diffusion conduits can have a valve to open and close the conduit, allowing and preventing, respectively, sample from flowing into the conduit. For example, in some embodiments, the sample chamber contains a porous membrane. To extract, concentrate, and/or purify the nucleic acid sample, the valves on both the waste conduit and reaction-diffusion conduits can be closed to allow the sample to interact with the membrane. To remove non-nucleic acid material, the valve on the waste conduit can be opened, while the valve on the reaction-diffusion conduit can remain closed. After the waste is removed, the valve on the waste conduit can be closed. Prior to amplification, the appropriate reactant mixture can be added to the sample chamber and the valve on the reaction-diffusion conduit can be opened, allowing diffusion of the amplified sample into the reaction-diffusion conduit. In some embodiments, the valve can be a passive valve. In other embodiments, the valve can be an active valve.

In some embodiments the nucleic acid amplification monitor further comprises a light source. Suitable light sources include, but are not limited to, light-emitting diode (LED), compact fluorescent lamp (CFL), filtered flash light of a cell phone camera, or incandescent.

The nucleic acid amplification monitor can further comprise an optical imager. Suitable optical imagers include, but are not limited to, a fluorescent microscope or a camera. In some aspects, the camera can be from a cellular telephone, smart-phone camera, tablet computer, or computer.

The nucleic acid amplification monitor can be operatively connected to a controller or computer.

In some embodiments, the nucleic acid amplification monitor further comprises a ruler along the length of the reaction-diffusion conduit.

The nucleic acid amplification monitor can further comprise a heat source. Suitable heat sources include a thermoelectric unit, an electric heater, an exothermic reactor, a laser, or any combination thereof. In some aspects, the heat source can provide a spatially varying temperature distribution along the length of the reaction-diffusion conduit. Such a heat source enables different temperatures to be applied to different regions of the reaction-diffusion conduit at different times. The temperature can be regulated with a phase change material. In some embodiments, the temperature gradient along the reaction-diffusion conduit can be linear. The temperature in the sample chamber can be different from the temperature in the reaction-diffusion conduit. In other embodiments, the temperature in the sample chamber can be the same as the temperature in the reaction-diffusion conduit.

In some embodiments, each of the chamber and the at least one reaction-diffusion conduit hold a blend of reactants for nucleic acid amplification. In other embodiments, each of the chamber and the at least on reaction-diffusion conduit are capable of holding a blend of reactants for nucleic acid amplification. The blend of reactants can comprise a plurality of primers and enzymes. In some embodiments, the blend of reactants can further comprise one or more types of reporters. Those skilled in the art would understand that numerous primers, enzymes, and reporters are suitable for nucleic acid amplification procedures. Suitable primers include, for example, DNA or RNA primers. The length of the primer (i.e. number of nucleotides) depends, in part, on the nucleic acid molecule to be amplified. Primers of any length suitable for nucleic acid amplification can be used herein. One skilled in the art would know that primers of nucleic acid amplification are used in sets or pairs—a forward or sense primer and a reverse or antisense primer. "Plurality of primers" and "primer sets" are used interchangeably herein and refer to at least one pair of primers. In some embodiments, the plurality of primers can be a pair of primers. In some embodiments, the plurality of primers can be 2 pairs of primers. In some embodiments, the plurality of primers can be more than 2 pairs of primers. Enzymes suitable for nucleic acid amplification include, but are not limited to, DNA polymerase, RNA-dependent DNA polymerase (reverse transcriptase), or DNA-dependent RNA polymerase (RNA polymerase). As used herein, the term "reporter" means any tag, label, or dye that can bind to, or intercalate within, the nucleic acid molecule to enable visualization of the nucleic acid molecule. Suitable reporters include, but are not limited to, fluorescent labels/tags/dyes and intercalating agents. The sample chamber and reaction-diffusion conduit may contain a mixture of primers engineered to be specific to various targets, enabling the concurrent amplification and detection of multiple targets. The sample chamber may contain universal primers to amplify all targets, while the reaction-diffusion conduits may contain primers for specific targets. In some embodiments, the universal primers in the sample chamber can be immobilized to prevent passage of the primers into the reaction-diffusion conduit. Primers can be immobilized to, for example, the sample chamber or something within the sample chamber that cannot pass into the reaction-diffusion conduit. The reaction-diffusion conduit may also contain reporters (molecular beacons) each engineered to bind to a specific target and each emitting at different range of the spectrum, allowing the detector, with appropriate filters, to image each target separately.

Other reactants include, but are not limited to, buffers and dNTPs.

The blend of reactants, or a portion thereof, can be pre-stored in the nucleic acid amplification monitor. In some embodiments, the blend of reactants, or a portion thereof, are pre-stored in the nucleic acid amplification monitor and are released upon an increase in temperature. For example, the blend of reactants can be released when the nucleic acid amplification monitor is heated to its operating temperature.

The blend of reactants can be liquid or can be in a form that is capable of forming a liquid upon a change in temperature, such as a gel or solid. For example, the blend of reactants can be encased in, embedded in, or surrounded by, a material that melts with increasing temperatures, such as, for example, paraffin.

In some embodiments, the nucleic acid amplification monitor can have at least two nuclemeters, each containing different primers. The primers can recognize the same nucleic acid molecule but differ in length. Alternatively, the primers can recognize different nucleic acid molecules and be the same length. Alternatively, the primers can recognize different nucleic acid molecules and be different lengths.

A single nuclemeter can have multiple reaction-diffusion conduits, at least two of said reaction-diffusion conduits containing different primers. For example, one reaction-diffusion conduit can contain a first plurality of primers and another reaction-diffusion conduit can contain a second plurality of primers, the second plurality of primers being different from the first plurality of primers. In such a device, the sample chamber can contain: a mix of a first plurality of primers and second plurality of primers; only a first plurality of primers; only a second plurality of primers; or a third plurality of primers.

In some embodiments, the blend of reactants in the sample chamber and the blend of reactants in the conduit are capable of amplifying different nucleic acid molecules. In some aspects, for example, the blend of reactants in the sample chamber and the blend of reactants in the conduit are capable of amplifying at least two different nucleic acid molecules.

In some embodiments, at least one of the reaction-diffusion conduits can contain at least one polymer. In some embodiments, at least one of the reaction-diffusion conduits and the sample chamber can contain at least one polymer. The presence of the polymer in the reaction-diffusion conduit or reaction-diffusion conduit and sample chamber can slow the diffusion of the amplified DNA and control the speed of propagation of the reaction front in the reaction-diffusion conduit, so that the diffusion may be easily monitored and/or quantified. In some embodiments, the at least one polymer can be a gel. In embodiments wherein the at least one polymer is a gel, the primers, enzymes, or both can be immobilized to the gel. In some embodiments, the polymer is a solid at an ambient temperature and a liquid at an amplification temperature. As used herein, "ambient temperature" refers to the temperature of the nucleic acid amplification monitor prior to the amplification procedure. Thus, prior to the amplification procedure, the polymer can be a solid. As the temperature increases at the start of or during the amplification procedure, the polymer can turn into a liquid. In other embodiment, the reaction-diffusion conduit contains gel.

The disclosed nucleic acid amplification monitors can be used for a number of purposes including, but not limited to, melting curve analysis, reverse transcription, identifying a nucleic acid in a sample sample, diagnosis, quantifying the number of nucleic acid molecules in a sample, and testing amplification reactants. In some embodiments, the sample chamber, reaction-diffusion conduit, or both are suitable for reverse transcription.

In some embodiments, the sample chamber and the reaction-diffusion conduit can be separate components.

Methods of Quantifying Nucleic Acid Amplification

Also disclosed herein are methods of quantifying nucleic acid amplification comprising amplifying a sample comprising a nucleic acid molecule in any of the devices or the nucleic acid amplification monitors disclosed herein to generate an amplified nucleic acid molecule and measuring a reaction-diffusion length of said amplified nucleic acid molecule through the one or more conduits, wherein reaction-diffusion length is proportional to the number of nucleic acid copies in the sample.

In some embodiments, amplifying the nucleic acid molecule comprises thermo-cycling. In other embodiments, amplifying the nucleic acid molecule comprises isothermal nucleic acid amplification.

Suitable methods for measuring a reaction-diffusion length of said amplified nucleic acid molecule include, but are not limiting to, measuring an electrical resistance, measuring a capacitance, measuring an absorption (for example, UV absorption), measuring an emission of a reporter, or any combination thereof. In some aspects, the reaction-diffusion length of said amplified nucleic acid molecule can be measured, for example, using a ruler. In some embodiments, the device or nucleic acid amplification monitor has a ruler along the length of the reaction-diffusion conduit. In other embodiments, the ruler is separate from the nuclemeter.

In some embodiments, quantifying the length of the emitting column in the reaction-diffusion column can be a function of nucleic acid concentration and time. By reading the length of the emitting column and the time elapsed from the onset of the amplification reaction, for example, one can determine the number of nucleic acid molecules in the sample. In other embodiments, quantification can be independent of time. For example, one can monitor two or more nuclemeters, at least one of which containing a known number of molecules (calibrator) and at least one containing an unknown number of nucleic acids (tester). The difference in the emission lengths of the tester and calibrator can enable one to determine the number of nucleic acid molecules in the tester, independent of the measurement time.

In some embodiments, the methods can further comprise comparing the reaction-diffusion length of the one or more reaction-diffusion conduits. For example, one or more of the reaction-diffusion conduits within the device can be compared to one or more of the reaction-diffusion conduits within the same device. Conversely, one or more of the reaction-diffusion conduits within the device can be compared to one or more reaction-diffusion conduits within a separate device. Comparison of the one or more reaction-diffusion conduits to reaction-diffusion conduits in the same device or in a separate device will allow one to evaluate, for example, the relative amount of one or more nucleic acid molecules. In other embodiments, the methods can further comprise comparing the reaction-diffusion length of the one or more reaction-diffusion conduits to a control. The control can be a reaction-diffusion conduit from the same device or from a separate device that contains a known quantity of a nucleic acid molecule, a nucleic acid molecule of a known identity, a sample from a subject having a known disease or condition, or any combination thereof. The quantity, identity, or sample from a subject may be indicative of the presence or absence of a disease or condition. The comparing can be used, for example, to determine: the presence or absence of a disease in a subject; the type or stage of a disease in a subject; or the effectiveness of therapy. For example, the one or more known nucleic acid molecules can be nucleic acid molecules that exhibit altered expression in the disease. In some aspects, the one or more nucleic acid molecules can be nucleic acid molecules whose expression is decreased in the disease. In some aspects, the one or more nucleic acid molecules can be nucleic acid molecules whose expression is increased in the disease. The reaction-diffusion length from the one or more known nucleic acid molecules can be indicative of a disease state. In some aspects, the reaction-diffusion length from the one or more known nucleic acid molecules can be indicative of a disease type. In some aspects, the reaction-diffusion length from the one or more known nucleic acid molecules can be indicative of a disease stage. In other embodiments, the reaction-diffusion length from the one or more known nucleic acid molecules is indicative of a normal (non-disease) state.

The one or more known nucleic acid molecules can be derived from cells, blood, serum, bacteria, or any other suitable source of a nucleic acid molecule. In some aspects, the nucleic acid molecules can be derived from cells from a subject suspected of having a disease. In some aspects, the nucleic acid molecules can be derived from the bacterial flora of a subject. Comparing the reaction-diffusion length of the sample to the reaction-diffusion length from one or more known nucleic acid molecules that are indicative of a disease state, a normal (non-disease) state, or both, can be used to determine if a subject has the disease state. Exemplary diseases include, for example, cancer.

Different reaction-diffusion conduits can store different primers specific to genes of interest. By comparing the reaction-diffusion lengths in different reaction-diffusion conduits, in which selected genes were amplified, with a library of gene expression profiles, one can determine, for example, the gene expression profile of the sample.

In some embodiments, the nucleic acid molecule is DNA. In some embodiments, the nucleic acid molecule is RNA. In embodiments wherein the nucleic acid molecule is RNA, the methods can further comprise, prior to the amplifying, reverse transcribing the RNA to generate cDNA.

The one or more known nucleic acid molecules can be markers of a disease. For example, the one or more known nucleic acid molecules can be nucleic acid molecules that exhibit altered expression in the disease. In some aspects, the one or more nucleic acid molecules can be nucleic acid molecules whose expression is decreased in the disease. In some aspects, the one or more nucleic acid molecules can be nucleic acid molecules whose expression is increased in the disease. For example, the one or more known nucleic acid molecules can be markers of cancer.

The results of the methods of obtaining a gene expression profile can be used, for example, to screen for a disease of interest, select an appropriate drug for a patient, or monitor therapy.

The disclosed methods can be used to determine the number of nucleic acid molecules in a sample by, for example, comparing the reaction-diffusion length in a reaction-diffusion conduit containing molecules from the sample to a reaction-diffusion length in a conduit having a known number of nucleic acid molecules. The control molecules may be pre-stored in the device or consist of house-keeping molecules in the sample. The disclosed methods can also be used to determine the relative expression of nucleic acid molecules in a sample by, for example, comparing the reaction-diffusion length to a reaction-diffusion conduit having a control sample and calculating the percentage or the reaction-diffusion length of the sample.

Methods of Identifying an Unknown Nucleic Acid Molecule

Also disclosed herein are methods of identifying an unknown nucleic acid molecule, comprising amplifying a sample comprising an unknown nucleic acid molecule in any of the devices or nucleic acid amplification monitors disclosed herein, wherein each of the at least one conduits contain a plurality of primers specific for a different known nucleic acid molecule and measuring a reaction-diffusion length within the reaction-diffusion conduit, wherein the presence of the reaction-diffusion length indicates that the sample having an unknown nucleic acid molecule comprises the known nucleic acid molecule to which the primers in the at least one conduit are specific and the extent of the reaction-diffusion length within the conduit indicates the number of the unknown nucleic acid molecules in the sample.

For example, the device or nucleic acid amplification monitor suitable for the disclosed methods of identifying an unknown nucleic acid molecule can contain one or more nuclemeters. The nuclemeters can have a plurality of reaction-diffusion conduits, each of said reaction-diffusion conduit containing a plurality of primers specific for a different known nucleic acid molecule. For example, each of the reaction-diffusion conduits can contain different primers for different viral nucleic acids. In some aspects, each of the reaction-diffusion conduits can contain different primers for different pathogens, such as bacteria, virus, and parasite nucleic acids. In other aspects, each of the reaction-diffusion conduits can contain different primers for different fungal nucleic acids. In yet other aspects, each of the reaction-diffusion conduits can contain different primers for different biomarkers which identify human disease. For example, each of the reaction-diffusion conduits can contain different primers for different cancer biomarkers. In some embodiments, a single nuclemeter can comprise a plurality of reaction-diffusion conduits, each reaction-diffusion conduit containing different primers for a variety of different pathogens, viruses, bacteria, fungus, human, animal, and plant diseases, or any combination thereof.

The disclosed methods of identifying an unknown nucleic acid molecule can be used, for example, in diagnosing a patient with an unknown infection or disease. For example, a nucleic acid sample can be isolated from a human, an animal, or a plant and added to the sample chamber of any one of the devices or nucleic acid amplification monitors disclosed herein, wherein the device or nucleic acid amplification monitor comprises at least one nuclemeter comprising at least one sample chamber and at least one reaction-diffusion conduit, said at least one conduit containing a plurality of primers specific for a different known nucleic acid molecule. Amplification will proceed in a reaction-diffusion conduit if that conduit contains primers specific for the unknown nucleic acid molecule. Amplification, which can be monitored by an emission, will indicate that the sample having an unknown nucleic acid molecule comprises at least a nucleic acid molecule for which the primers are specific.

In addition to identifying unknown nucleic acid samples, the disclosed methods can be used to determine a number of nucleic acid molecules in the unknown nucleic acid sample. For example, in some embodiments, the method comprises determining the difference in length of reaction-diffusion from a nuclemeter having a sample having a known quantity of a nucleic acid and a nuclemeter having a sample having an unknown nucleic acid molecule, wherein the difference in the length of the reaction-diffusion between the known quantity of a nucleic acid molecule and the sample having an unknown nucleic acid molecule indicates a number of nucleic acid molecules in the sample having the unknown nucleic acid molecule.

Suitable methods for measuring a reaction-diffusion length of said amplified nucleic acid molecule include, but are not limiting to, measuring an electrical resistance, measuring a capacitance, measuring an absorption (for example, UV absorption), measuring an emission of a reporter, or any combination thereof. In some aspects, for example, the length of the reaction-diffusion can be determined by using a ruler. In some embodiments, the device or nucleic acid amplification monitor has a ruler along the length of the reaction-diffusion conduit. In other embodiments, the ruler is separate from the nuclemeter.

Systems for Monitoring Nucleic Acid Amplification

Further disclosed are systems for monitoring nucleic acid amplification comprising a nuclemeter, an optical imager, and a heat source. The nuclemeter comprises an sample chamber and at least one reaction-diffusion conduit in fluid communication with the sample chamber. In some embodiments, each of the sample chamber and the at least one reaction-diffusion conduit hold a blend of reactants for nucleic acid amplification. In other embodiments, each of the sample chamber and the at least one reaction-diffusion conduit are capable of holding a blend of reactants for nucleic acid amplification.

Any of the nuclemeters disclosed herein are suitable for the disclosed system.

The system can further comprise a controller, an output device, or a combination thereof.

The sample chamber can have a size and shape suitable for containing a nucleic acid amplification reaction.

Each of the optical imager, heat source and output device can be operably controlled by the controller.

EXAMPLES

Methods

Nuclemeter Chip Fabrication

Figure 1:
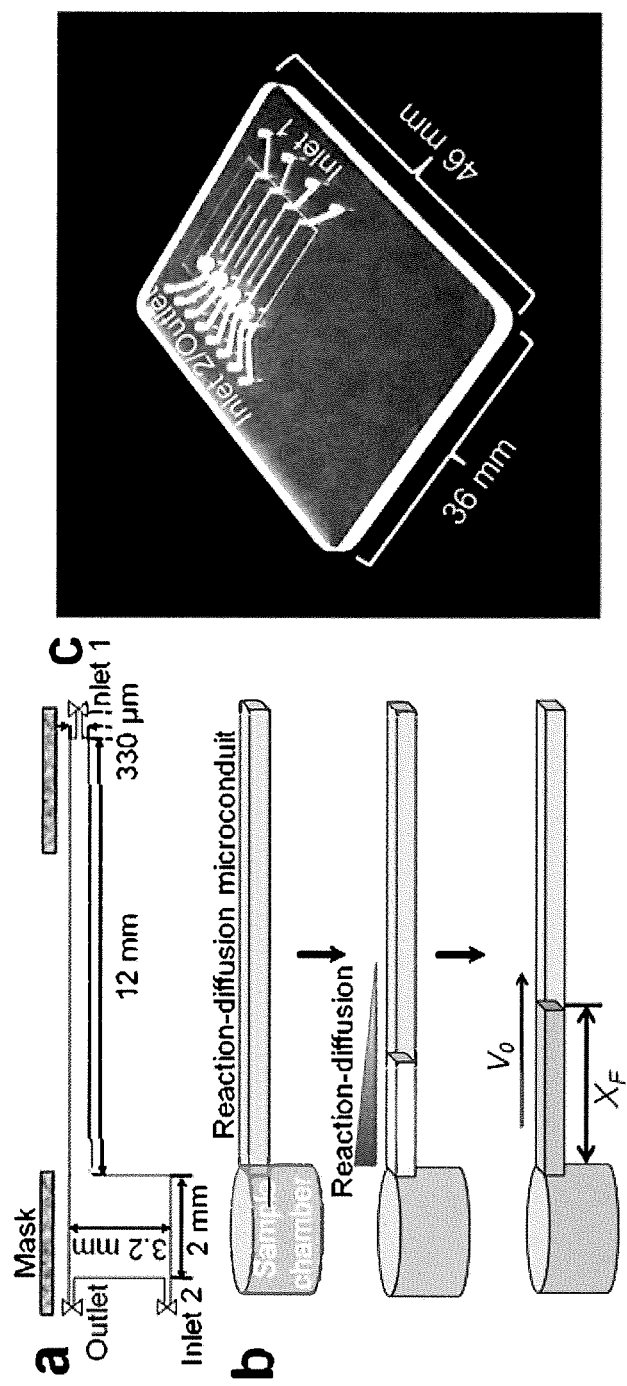
FIG. 1, comprising
Figure 1:
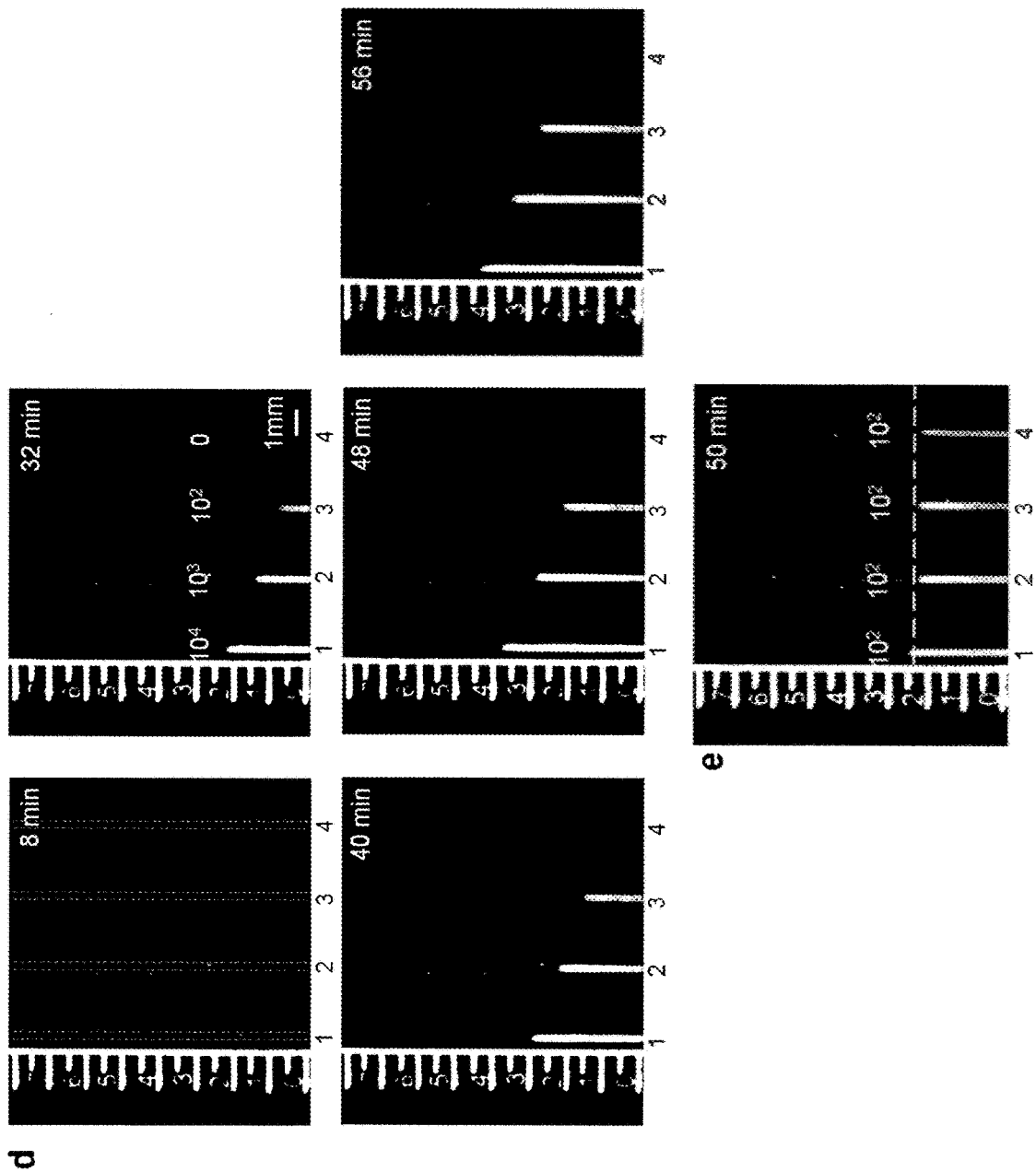

The 46 mm long×36 mm wide×3.0 mm thick, Poly (methyl methacrylate) (PMMA, Acrylic glass) body of the chip was milled with a precision, computer-controlled (CNC, HAAS Automation Inc., Oxnard, CA) milling machine (FIG. 1C). An inlet port and an exit port were connected to the sample chamber and a third port was connected to the distal end of the microconduit (FIG. 1A). After milling, the chip body was sonicated in 100% ethanol for 15 minutes, rinsed with water, and air-dried at room temperature. To eliminate any RNase and DNase that could degrade nucleic acids or interfere with enzymatic reactions, the chip body was dipped in Decon™ ELIMINase™ decontaminant (Thermo Fisher Scientific Inc., Walthman, MA) for 2 minutes, rinsed twice with sterile molecular biology-grade water (Thermo Fisher Scientific Inc.), and air-dried at room temperature.

The chip body was ceiled and floored with PMMA film (top) and PCR Sealers™ tape (bottom), respectively (FIG. 3). Both were cut with a $CO_2$ laser (Universal Laser Systems). The top PMMA film was solvent-bonded to the chip body with acetonitrile (Sigma-Aldrich) at room temperature. The bonded chip was heated overnight (Isotemp Vacuum Oven Model 280A, Fisher Scientific Inc., Pittsburgh, PA) at 55° C. to remove any residual solvent. Finally, the PCR Sealers™ tape was used to seal the bottom of the chip.

HIV RNA Purification from Plasma Samples

Viral RNA was extracted from HIV-1 standards (AcroMetrix® HIV-1 High Control, Benicia, CA) with QIAamp Viral RNA Mini Kit (Qiagen, Valencia, CA) according to the manufacturer's protocol. Briefly, 140 µL of virus suspension was lysed with 560 µL virus lysis buffer containing carrier RNA. 560 µL ethanol was added to the lysate and the mixture was centrifuged in a spin column (630 µL aliquots) at 10,000 rpm for 2 minutes. Prior to eluting the HIV viral RNA, wash buffers were loaded into the spin column and centrifuged at 14,000 rpm for 5 minutes. The RNA was eluted with 60 µL of elution buffer. Negative controls were prepared from a de-identified HIV-negative plasma sample (provided by the Penn Center for AIDS Research CFAR with the Institutional Review Board approval (protocol: 814752)) using the same extraction procedures as described above.

RT-LAMP Reagents

The RT-LAMP primers were designed as described in Curtis, K. A., Rudolph, D. L. & Owen, S. M. J. Virol. Meth. 151, 264-270 (2008) at the Center for Disease Control and Prevention (CDC) and were synthesized by Sigma-Aldrich. The real-time benchtop RT-LAMP experiments were carried out with 15 µL reaction volumes. The reaction mixture consisted of 0.2 µM of F3 and B3, each; 0.8 µM Loop F and Loop B, each; and 1.6 µM of FIP and BIP, each, 1.25 U AMV reverse transcriptase (Life Technologies, Carlsbad, CA); 0.53×EvaGreen dye (Biotium, Hayward, CA); 0.04% (w/v) hydroxypropyl-methyl-cellulose (HPMC); and 9 µL Isothermal Master Mix (ISO-001nd, OptiGene, Horsham, UK).

The HPMC was dissolved in Isothermal Master Mix, centrifuged at 10,000 rpm for 2 minutes, and filtered through a Corning Costar® Spin-X® centrifuge tube equipped with cellulose acetate membrane filters with a pore size of 0.45 µm to remove any traces of insoluble HPMC.

A ten-fold dilution series of HIV viral RNA extracted from a HIV-1 standard panel and a negative control without template prepared from a HIV-negative plasma sample were tested in parallel. The real-time, "tubed-based" RT-LAMP was carried out in a Peltier Thermal Cycler PTC-200 (Bio-Rad DNA Engine, Hercules, CA). Reactions were carried out at 62.5° C. for 60 minutes with real-time fluorescence monitoring. Real-time RT-LAMP results were analyzed and the threshold time $C_t$ (the time needed for the emission intensity to exceed a predetermined value) was obtained.

Device Operation

5 µL of RT-LAMP master mixture, comprised of all the reagents necessary for the RT-LAMP and 0.04% HPMC (excluding the HIV RNA template), was inserted into each reaction-diffusion microconduit through inlet port 1 (FIGS. 1A and 1C). Then, inlet ports 1 of all four nuclemeters were sealed with PCR Sealers™ tape. Next, 15 µl of RT-LAMP master mixture and HIV RNA template of various concentrations were injected into the sample chambers through the inlet ports 2 (FIGS. 1A and 1C). Subsequently, both the inlet ports 2 and outlet ports were sealed with PCR Sealers™ tape to minimize evaporation during the amplification process. The nuclemeter chip was placed on a custom, portable heater and incubated at 62.5° C. for about 60 minutes to enable isothermal amplification.

Portable Processor for RT-LAMP

The custom made, portable processor (FIGS. 5 and 6) for the nuclemeter consisted of a chip holder equipped with a flexible, polyimide-based, thin film heater (Model HK5572R7.5L23A, Minco Products, Inc., Minneapolis, MN) (inset in FIG. 6A), an electronic circuit board, and a thermocouple positioned at the interface between the thin film heater and the nuclemeter chip. When the nuclemeter chip, filled with LAMP master mixture, was inserted into the processor, the sample chambers and diffusion conduits were in thermal contact with the thin film heater.

To thermally calibrate the device, a calibration chip with a type-K thermocouple (Omega Engr., each wire 75 mm in diameter, and a junction diameter of 170 µm) was constructed in the reaction-diffusion conduit. The sample chambers and reaction-diffusion conduits were filled with water. The thermocouple reading was monitored with a HH506RA multilogger thermometer (Omega Engr., Stamford, CT, USA). In addition, an infrared image of the heated microfluidic chip was taken with an infrared thermography camera T360 (FLIR Systems, Wilsonville, USA) to evaluate temperature uniformity (FIG. 6B).

Endpoint, Fluorescence Image for Quantitative Detection

The fluorescence excitation and emission imaging were carried out with a handheld, USB-based, fluorescence microscope (AM4113T-GFBW Dino-Lite Premier, AnMo Electronics, Taipei, Taiwan) (FIGS. 5 and 6). The USB-based, fluorescence microscope has built-in, filtered blue LEDs for excitation, a 510 nm emission filter, and a CCD camera for fluorescence imaging. The microscope was interfaced with a computer through a USB interface. Images were acquired with a DinoCapture 2.0 software program. The images were processed with MatLab™ software to remove background noise and uneven illumination effects. A normalized and averaged fluorescence intensity signal for each lane was extracted from each processed image. The locations of the reaction fronts of different samples were directly read out by eye with the fluorescence ruler (FIG. 6C).

As an alternative to fluorescent dye to indicate the length of the reaction zone, bioluminescence can be used (FIG. 14). The bioluminescent real time reporter (BART) was included with the reagents. During DNA amplification in microconduits, the reporter emits visible light at the reaction front, providing an indication of the position of the reaction front. When bioluminescence is used, there is no need for excitation, eliminating any background emission. The emission consists of white light that can be recorded directly by charged coupled device camera, cell phone camera or by eye (FIG. 14).

Image Processing and Analysis

Images were processed post-acquisition to facilitate comparison with numerical simulations. Initially, the noise was removed from all images using a low pass filter. Then, the images were corrected by applying the following scaling:

$$I_c = \frac{I_r - I_b}{I_f - I_b},$$

where $I_c$ is the corrected emission intensity, $I_r$ is the filtered intensity, $I_r$ is the background intensity, and $I_f$ is the flat maximum intensity. The background intensity is the average of the first five video frames when there are too few amplicons to generate a significant signal. The maximum intensity was obtained from the last frame acquired. The intensity signal at each position x was averaged along the width of the conduit. All image processing and mathematical calculations were performed with MatLab.

Results

The disclosed nuclemeters enable monitoring and endpoint quantitative detection of amplified nucleic acids based on the position of a reaction front. The nuclemeter is comprised of a sample chamber and a reaction-diffusion conduit, containing all the reagents needed for enzymatic amplification, polymeric additive HPMC to slow diffusion, as well as intercalating dye reporter (FIG. 1A-C). A sample laden with target nucleic acids was introduced into the sample chamber and the amplification reaction was triggered thermally. As time progresses, amplicons diffused into the conduit, where they continue to react and amplify. After a certain time threshold, the conduit consisted of two distinct regions (FIG. 1B): the bright, left segment ($0 < x < X_F$), where the amplification reaction had already generated a sufficient number of amplicons to emit detectable fluorescence emission; and the dark, right section ($x > X_F$) into which amplicons had yet to diffuse. As time proceeded, the reaction front ($X_F$), separating between the bright and dark regions, propagated to the right. Without intent to be bound by theory, it is believed that the position of the reaction front indicates target analyte concentration. Many nuclemeters can be housed on a single chip and imaged simultaneously for concurrent monitoring of multiple amplification processes, calibration standards, and controls.

Polymethyl methacrylate (PMMA) chips consisting of four nuclemeters (FIG. 1C and FIG. 3) were fabricated. Each nuclemeter consisted of a 2 mm diameter×2.80 mm deep sample well (~9 μL) connected to a 330 μm wide×330 μm deep×12 mm long reaction-diffusion conduit (FIG. 1A and FIG. 4). Reverse transcription, loop-mediated isothermal amplification (RT-LAMP), as described in Notomi, T. et al. Nucleic Acids Res. 28, E63 (2000) and Tomita, N., Mori, Y., Kanda, H. & Notomi, T. Nat. Protoc. 3, 877-882 (2008), was used to quantify HIV viral load. Samples containing 0, $10^2$, $10^3$, and $10^4$ HIV-1 RNA molecules were inserted into the sample wells (FIG. 1B) and incubated at 62.5° C. using a custom, portable, processor (FIGS. 5 and 6). The emission from the reaction-diffusion conduits was recorded using an USB fluorescent microscope (FIG. 1D). The position of the reaction front ($X_F$) was quantified with a ruler affixed on the processor (FIG. 6C). At any given time, the greater the number of target molecules, the larger $X_F$. Thus, with appropriate calibration, the number of initial target molecules can be inferred from $X_F$. Although $X_F$ increases as time increases at any target concentration, the differences between $X_F$ values associated with different concentrations are time-independent.

The reproducibility of the nuclemeter was evaluated by introducing identical target concentrations ($10^2$ copies HIV-1 RNA) into all four sample wells (FIG. 1E). All four conduits exhibited nearly identical $X_F$ (±4.5%) at any given time. Furthermore, the limits of detection were tested by reducing the number of target molecules. As few as 50 RNA copies were consistently detected, comparable to the performance of a benchtop RT-LAMP (FIG. 7).

Figure 2:
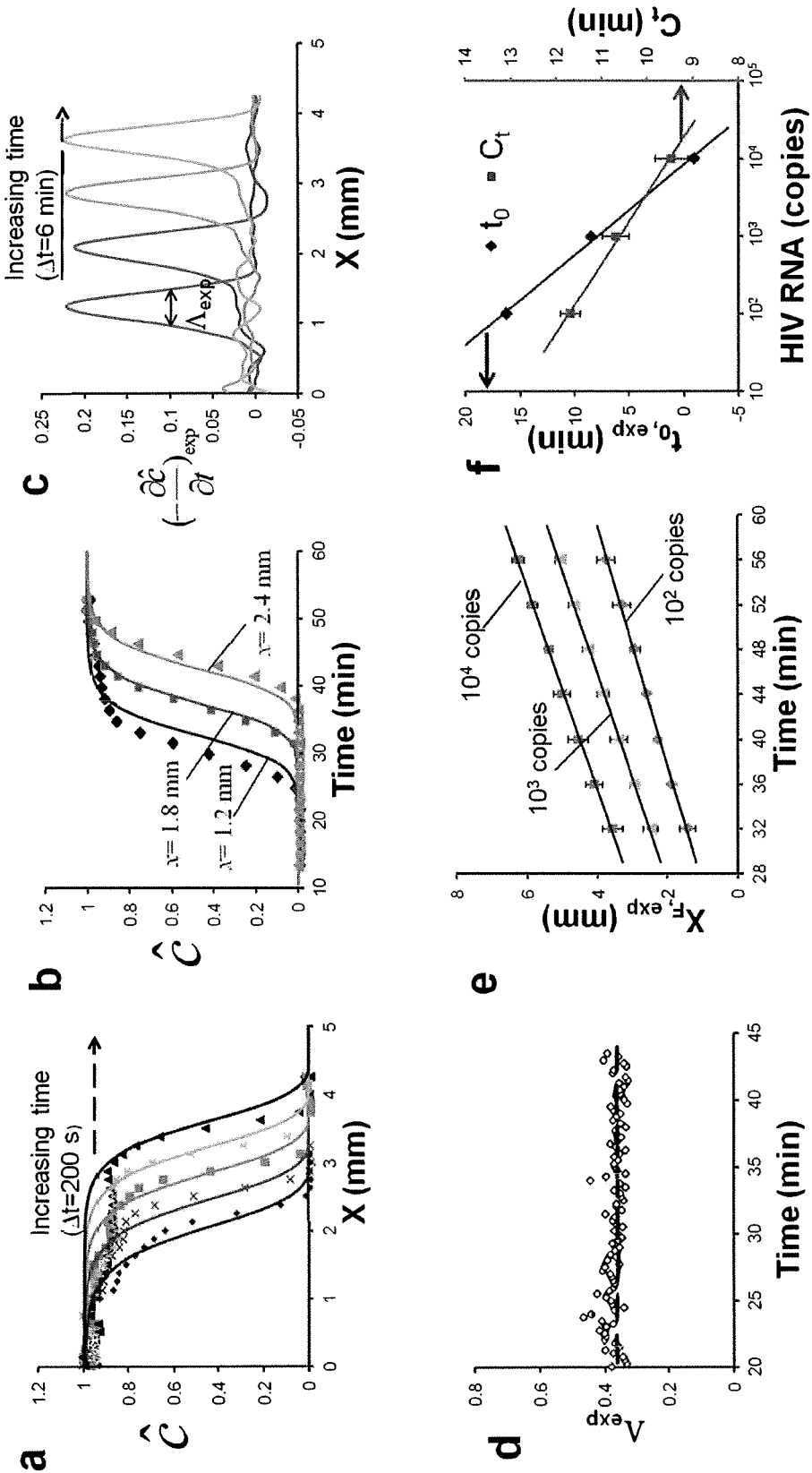
FIG. 2, comprising
Figure 2:
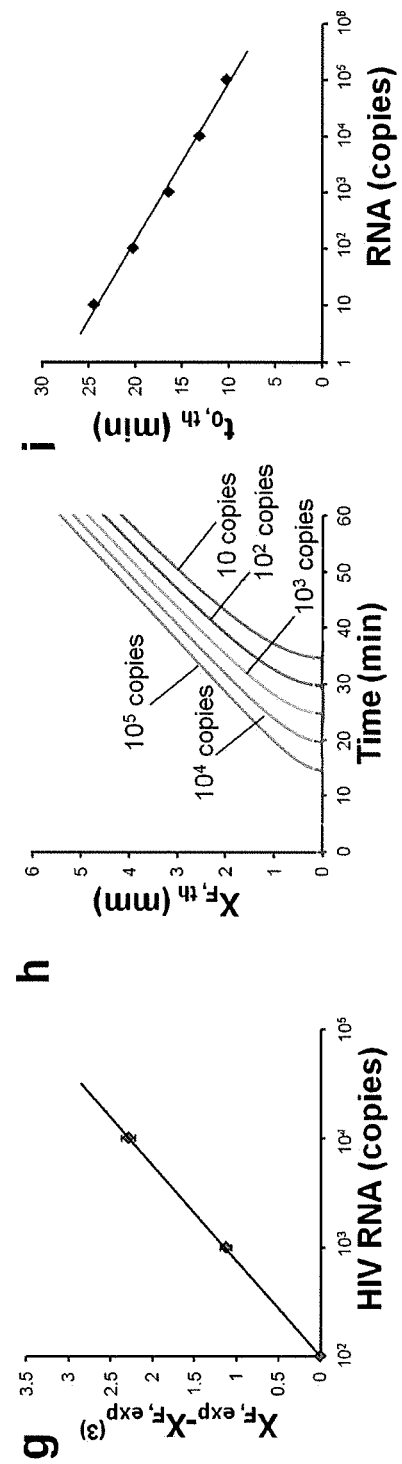

FIG. 2 illustrates the experimental data and compares it with the predictions of a simple theoretical model. The emission intensity was taken to be proportional to the amplicons' concentration c(x,t), assumed uniform in each cross-section of the conduit. FIG. 2A depicts $ĉ=c/c_{max}$ as a function of position x at various times t. The lines and symbols correspond, respectively, to predictions and experimental data. The location of the reaction front $X_F(t)$ was defined as the position at which $ĉ(X_F,t)=0.5$. When $x<X_F$, $ĉ \sim 1$ and the amplification reaction is nearly complete (the regions with fluorescent emission in FIG. 1D). When $x>X_F$, $ĉ \sim 0$ and no amplification has yet occurred (the dark regions in FIG. 1d). FIG. 2B depicts $ĉ$ as a function of time at various positions x. An observer located at position x will not see a signal until after a certain time delay. FIG. 2C depicts the experimentally-determined rate of the reaction $$\left(-\frac{\partial ĉ}{\partial t}\right)_{exp}$$

as a function of position (x) at various times. The rate of the reaction resembles a propagating peak that travels at a fixed velocity $v_0$. The peak's width at midheight (Λ) did not vary with time (FIG. 2D), i.e., the reaction front is non-dispersive.

The position of the reaction front $X_F(t)$ was depicted as a function of time when the number of target molecules is $10^2$, $10^3$, and $10^4$ (FIG. 2E, n=3). For sufficiently large times, $t > t_1 > t_0$, the experimental data correlates well with straight lines ($R^2=0.998$).

$$X_F(t)=v_0(t-t_0), \qquad (1)$$

Where t (s) is the observation time, $t_0$ (s) is the intercept with the horizontal axis, and $t_1$ (s) is the delay time until a visible signal is observed. All the lines in FIG. 2E have nearly the same slope, indicating that the front propagates at a nearly constant speed of $v_0^{exp}=1.73\pm0.15$ μm/s (n=9) independent of target concentration. In contrast, $t_0$ decreases as the target concentration increases (FIG. 2F), playing a similar role to the threshold time ($C_t$) in a standard real-time quantitative amplification. For comparison, $C_t$ is also shown in FIG. 2F (see also FIG. 8).

$$t_0 = A - B \log(c_0), \qquad (2)$$

where A and B are constants and $c_0$ is the number of target molecules ($R^2=0.996$).

Although the position of the front $X_F$ is time-dependent, the distances between any two fronts associated with different numbers of target molecules are not (FIG. 9). Thus, time-dependence can be eliminated by subtracting the position of the front of a calibration lane ($X_F^{(c)}$) containing a known target concentration from that of the test lane. To demonstrate this, variables associated with lanes 1, 2, and 3

(FIG. 1D) were denoted with superscripts 1, 2, and 3. FIG. 2G depicts $X_F^{(1)}$–$X_F^{(3)}$ as a function of the number of target molecules $c_0^{(i)}$. It is observed that all the data collapses to a single straight line (n=15, $R^2$=0.99), eliminating any explicit dependence on the time at which $X_F$ was measured. Thus, in the presence of a calibration nuclemeter (c), $$\Delta X_F^{(i)} = X_F^{(i)}(t) - X_F^{(c)}(t) = v_0(t_0^{(c)} - t_0^{(i)}). \tag{3}$$

In the presence of one or more calibration nuclemeters, one can rely on the differences among reaction front positions to determine target concentration, independent of measurement time. Although not essential, a device could include at least one calibration nuclemeter. The calibration nuclemeters can, of course, also serve as positive controls. With the aid of equation (2), equation (3) can be rewritten to express explicitly the dependence of $\Delta X_F$ on target analyte concentration.

$$\Delta X_F^{(i)} = v_0 B \log\left(\frac{c_0^{(i)}}{c_0^{(c)}}\right). \tag{4}$$

When a monitoring device includes two calibration nuclemeters c1 and c2 with known target concentrations c0I(1) and c02(2), respectively, the difference of the emission lengths of the two calibration columns is $$\Delta X_F^{(c)} = X_F^{(c2)} - X_F^{(c1)} = v_0 B \log\left(\frac{c_0^{(c2)}}{c_0^{(c1)}}\right)$$

and $$\Delta X_F^{(i)} = \Delta X_F^{(c)} \frac{\log(c_0^{(i)}) - \log(c_0^{(c1)})}{\log(c_0^{(c2)}) - \log(c_0^{(c1)})}.$$

A simple reaction-diffusion mathematical model to simulate the experiment was proposed to gain further insight into the operation of the nuclemeter. The amplicon production during enzymatic amplification was approximated with the production term $kc_{max}\hat{c}(1-\hat{c})$, where the reaction rate constant k~0.008 s$^{-1}$ was determined empirically by fitting theoretical predictions with real time RT-LAMP amplification curves (See below—estimation of the reaction rate constant). $c_{max}$ was estimated at ~1.1×10$^{-10}$ mol/m$^3$. The variable c in the theory plays the same role as I in the experiment. The reaction diffusion process in the nuclemeter was modeled with the dimensionless equation $$\frac{\partial \hat{c}}{\partial \hat{t}} = \frac{\partial^2 \hat{c}}{\partial \hat{x}^2} + \hat{c}(1-\hat{c}) \; (-\hat{d} < \hat{x} < \infty). \tag{5}$$

In the above, distance was scaled with $\sqrt{D/k}$ and time with k$^{-1}$. The diffusion coefficient D~10$^{-10}$ m$^2$/s was estimated by monitoring the diffusion of labeled primers in the conduit in the absence of amplification reaction (See below—Estimating the Diffusion Coefficient (D)). The boundary and interfacial conditions are:

$$\frac{\partial \hat{c}(-\hat{d},\hat{t})}{\partial \hat{x}} = 0; \hat{c}(0^-,\hat{t}) - \hat{c}(0^+,\hat{t}) = \frac{\partial \hat{c}(0^-,\hat{t})}{\partial \hat{x}} - \frac{\partial \hat{c}(0^+,\hat{t})}{\partial \hat{x}} = 0$$

(the interface between the well and the conduit); and c(∞, t)=0. The initial conditions are $\hat{c}(\hat{x},0)=\hat{c}_0$ when $-\hat{d}<\hat{x}<0$ (sample well) and $\hat{c}(\hat{x},0)=0$ when $0<\hat{x}<\infty$ (conduit).

The predictions of equation (5) (solid lines in FIGS. 2A and B) closely resemble the experimental data. FIG. 2H depicts the position of the predicted reaction front as a function of time for different initial concentrations $\hat{c}$. Although at short times, the front velocity varies as a function of $\hat{c}$, soon enough all the curves asymptote to straight lines with a slope independent of time and the initial target concentration. The dimensionless predicted reaction front velocity is 2. The dimensional predicted reaction front velocity $v_0^{theory}$=2∞kD~1.8 µm/s is very close to the experimentally measured one. Moreover, consistent with experiments, the theory predicts a constant reaction front velocity independent of target concentration. When $\hat{t}>\hat{t}_1>\hat{t}_0$, the front location can be estimated with equation (1), where $\hat{t}$ depends on the initial concentration through equation (2). FIG. 2I depicts the predicted $t_0$ as a function of the number of target molecules using an estimated value of $c_{max}$. FIG. 2I is in qualitative agreement with the experimental data of FIG. 2F.

Estimation of the Reaction Rate Constant

To estimate the reaction rate constant, LAMP amplification was carried out in the nuclemeter's sample well (FIG. 10). The amplification process was approximated with $$\frac{dc}{dt} = kc\left(1 - \frac{c}{c_{max}}\right) \tag{6}$$

where c is the concentration (mol/m$^3$), k (s$^{-1}$) is the reproductive parameter, and $c_{max}$ (mol/m$^3$) is the saturation concentration. The fluorescence emission intensity was assumed to be proportional to the concentration. This assumption is not critical and equation (6) could have been formulated in terms of the emission intensity instead of the concentration. It is convenient to introduce the normalized concentration $$\hat{c} = \frac{c}{c_{max}}.$$

Accordingly, equation (6) reduces to with the initial condition:

$$\frac{d\hat{c}}{dt} = k\square\hat{c}\square(1-\hat{c}) \tag{7}$$

$$\hat{c}(0)=\hat{c}_0 \tag{8}$$

Equation (7) with initial condition (8) admits the solution:

$$\hat{c}(t) = \frac{\hat{c}_0}{(1-\hat{c}_0)\exp(-kt) + \hat{c}_0}. \tag{9}$$

By minimizing the discrepancy between the predictions of equation (9) and the experimental data, the reaction rate constant k and $\hat{c}$ and were estimated. FIG. 10D depicts the predictions of equation (9) with the optimal estimate k=0.008 s$^{-1}$ and $\hat{c}$=0.006 (solid lines) along with the experimental data (symbols). The number of target molecules is 10$^3$ copies.

Estimating the Diffusion Coefficient (D)

To estimate the diffusion coefficient of nucleic acids in the HPMC polymer solution, oligonucleotides tagged with a fluorescent dye (HEX-GGTGTCTCATTGTTTATACTA) were introduced into the sample well and monitored the nucleic acid diffusion in the microconduit as a function of time (FIG. 11A). This experiment was carried out at the LAMP incubation temperature of 62.5° C., but in the absence of enzymes so that no amplification took place. The normalized signal intensity (normalized concentration) is depicted (dashed lines) in FIG. 10B as a function of position along the conduit at various times.

The concentration distribution was modeled with a diffusion equation in a semi-infinite medium:

$$\frac{\partial \hat{c}}{\partial t} = D \frac{\partial^2 \hat{c}}{\partial x^2} \quad 0 \leq t \leq \tau, x \geq 0 \tag{10}$$

with the initial and boundary conditions $$\hat{c}(0,t)-1=\hat{c}(\infty,t)=\hat{c}(x,0)=0 \tag{11}$$

In the above, $$\hat{c} = \frac{c}{c(0, t)}$$

where c(0,t) is assumed to be time-independent. Since the volume of the sample chamber far exceeds the volume of the conduit, the error introduced by assuming that c(0,t) remains constant throughout the process is quite small, as has been verified both by scaling analysis and by obtaining a more accurate solution for equation (10) that allows for time-dependence of c(0,t) as mandated by mass conservation.

Equations (10) and (11) admit the classical solution $$\hat{c} = \text{erfc}\left(\frac{x}{2\sqrt{Dt}}\right). \tag{12}$$

Using the MatLab Optimization toolbox (The MathWorks, Inc., Natick, MA), it was observed that D~10$^{-10}$ m$^2$s$^{-1}$ minimized the discrepancy between the predictions of equation (12) and the experimental data. The predictions of equation (12) with the optimal D are depicted (dashed lines) along with the experimental data (symbols) in FIG. 11B.

Disclosed herein are devices and endpoint methods for the quantification of nucleic acids undergoing enzymatic amplification. Unlike traditional quantitative fluorescence enzymatic amplification detection, the disclosed devices and methods do not require continuous monitoring of the amplicons and is based on inferring the number of target nucleic acid molecules from the position of the amplification reaction front. The nuclemeter requires only a single image to quantify the nucleic acid at a prescribed time or, in the presence of a calibration column, at any time. The nuclemeter is compatible with multiplexing, allowing low-cost, high throughput nucleic acid screening, and it may be readily combined with modules for nucleic acid isolation, concentration, purification, and self-heating to facilitate inexpensive non-instrumented, quantitative, on-site molecular detection.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

EMBODIMENTS

The following list of embodiments is intended to complement, rather than displace or supersede, the previous descriptions.

Embodiment 1

A device for monitoring nucleic acid amplification comprising a nuclemeter comprising a sample chamber and at least one reaction-diffusion conduit in fluid communication with the sample chamber, each of the sample chamber and the conduit being capable of holding a blend of reactants for nucleic acid amplification.

Embodiment 2

The device of embodiment 1, wherein the sample chamber has a size and shape suitable for containing a nucleic acid amplification reaction.

Embodiment 3

The device of embodiment 1 or 2, wherein the sample chamber and the conduit are separated with a barrier.

Embodiment 4

The device of any one of the previous embodiments, wherein the barrier is removable, is comprised of a material that degrades, dissolves, or melts, is movable, or any combination thereof.

Embodiment 5

The device of any one of the previous embodiments, having a plurality of reaction-diffusion conduits in fluid communication with the sample chamber.

Embodiment 6

The device of any one of the previous embodiments, having a plurality of sample chambers, each sample chamber having at least one reaction-diffusion conduit in fluid communication therewith.

Embodiment 7

The device of embodiment 6, wherein at least some of the sample chambers have a plurality of reaction-diffusion conduits in fluid communication therewith.

Embodiment 8

The device of embodiment 7, at least one sample chamber having a known quantity of a preselected, target nucleic acid molecule.

Embodiment 9

The device of any one of the previous embodiments, the sample chamber having a porous membrane for nucleic acids extraction, concentration, and purification.

Embodiment 10

The device of any one of the previous embodiments, further comprising a waste conduit, a light source, an optical imager, a heat source, or any combination thereof.

Embodiment 11

The device of embodiment 10, wherein the optical imager is a fluorescent microscope or a camera.

Embodiment 12

The device of embodiment 10 or 11, wherein the heat source is a thermoelectric unit, an electrical heater, an exothermic reactor, or a laser.

Embodiment 13

The device of embodiment 12, wherein the heat source provides a spatially varying temperature distribution along the length of the reaction-diffusion conduit.

Embodiment 14

The device of embodiment 12 or 13, wherein the temperature is regulated with a phase change material.

Embodiment 15

The device of any one of embodiments 12-14, wherein the temperature in the sample chamber is different from the temperature in the conduit.

Embodiment 16

The device of any one of the previous embodiments, said device being operatively connected to a controller or computer.

Embodiment 17

The device of any one of the previous embodiments, further comprising a ruler along the length of the reaction-diffusion conduit.

Embodiment 18

The device of any one of the previous embodiments, further comprising a blend of reactants.

Embodiment 19

The device of embodiment 18, wherein the blend of reactants comprises a plurality of primers and enzymes.

Embodiment 20

The device of embodiment 19, having at least two nuclemeters, each containing different primers.

Embodiment 21

The device of embodiment 19, wherein the nuclemeter has multiple reaction-diffusion conduits, at least two of said reaction-diffusion conduits containing different primers.

Embodiment 22

The device of any one of the previous embodiments, wherein the reaction diffusion conduit contains at least one polymer.

Embodiment 23

The device of any one of the previous embodiments, wherein the sample chamber contains at least one polymer.

Embodiment 24

The device of embodiment 23, wherein the at least one polymer is a gel.

Embodiment 25

The device of embodiment 24, wherein the primers, enzymes, or both are immobilized to the gel.

Embodiment 26

The device of any one of embodiments 23-25, wherein the polymer is a solid at an ambient temperature and a liquid at an amplification temperature.

Embodiment 27

The device of any one of the previous embodiments, wherein the sample chamber, reaction-diffusion conduit, or both are suitable for reverse transcription.

Embodiment 28

A nucleic acid amplification monitor comprising a substrate and, on or forming a part of the substrate, a plurality of nuclemeters, each nuclemeter comprising an sample chamber and at least one reaction-diffusion conduit in fluid communication with the chamber, each of the chamber and the conduit being capable of holding a blend of reactants for nucleic acid amplification.

Embodiment 29

The nucleic acid amplification monitor of embodiment 28, wherein the sample chamber has a size and shape suitable for containing a nucleic acid amplification reaction.

Embodiment 30

The nucleic acid amplification monitor of embodiment 28 or 29, wherein the sample chamber and the conduit are separated with a barrier.

Embodiment 31

The nucleic acid amplification monitor of embodiment 30, wherein the barrier is removable, is comprised of a material that degrades, dissolves, or melts, is movable, or any combination thereof.

Embodiment 32

The nucleic acid amplification monitor of any one of embodiments 28-31, having a plurality of reaction-diffusion conduits in fluid communication with the sample chamber.

Embodiment 33

The nucleic acid amplification monitor of any one of embodiments 28-32, having a plurality of sample chambers, each sample chamber having at least one reaction-diffusion conduit in fluid communication therewith.

Embodiment 34

The nucleic acid amplification monitor of embodiment 33, wherein at least some of the sample chambers have a plurality of reaction-diffusion conduits in fluid communication therewith.

Embodiment 35

The nucleic acid amplification monitor of embodiment 34, at least one sample chamber having a known quantity of a preselected, target nucleic acid molecule.

Embodiment 36

The nucleic acid amplification monitor of any one of embodiments 28-35, the sample chamber having a porous membrane for nucleic acids extraction, concentration, and purification.

Embodiment 37

The nucleic acid amplification monitor of any one of embodiments 28-36, further comprising a waste conduit, a light source, an optical imager, a heat source, or any combination thereof.

Embodiment 38

The nucleic acid amplification monitor of embodiment 37, wherein the optical imager is a fluorescent microscope or a camera.

Embodiment 39

The nucleic acid amplification monitor of embodiment 37 or 38, wherein the heat source is a thermoelectric unit, an electrical heater, an exothermic reactor, or a laser.

Embodiment 40

The nucleic acid amplification monitor of embodiment 39, wherein the heat source provides a spatially varying temperature distribution along the length of the reaction-diffusion conduit.

Embodiment 41

The nucleic acid amplification monitor of embodiment 39 or 40, wherein the temperature is regulated with a phase change material.

Embodiment 42

The nucleic acid amplification monitor of any one of embodiments 39-41, wherein the temperature in the sample chamber is different from the temperature in the conduit.

Embodiment 43

The nucleic acid amplification monitor of any one of embodiments 28-42, said device being operatively connected to a controller or computer.

Embodiment 44

The nucleic acid amplification monitor of any one of embodiments 28-43, further comprising a ruler along the length of the reaction-diffusion conduit.

Embodiment 45

The nucleic acid amplification monitor of any one of embodiments 28-44, further comprising a blend of reactants.

Embodiment 46

The nucleic acid amplification monitor of embodiment 45, wherein the blend of reactants comprises a plurality of primers and enzymes.

Embodiment 47

The nucleic acid amplification monitor of embodiment 46, wherein the nuclemeter has multiple reaction-diffusion conduits, at least two of said reaction-diffusion conduits containing different primers.

Embodiment 48

The nucleic acid amplification monitor of any one of embodiments 28-47, wherein the reaction diffusion conduit contains at least one polymer.

Embodiment 49

The nucleic acid amplification monitor of embodiment 48, wherein the at least one polymer is a gel.

Embodiment 50

The nucleic acid amplification monitor of embodiment 49, wherein the primers, enzymes, or both are immobilized to the gel.

Embodiment 51

The nucleic acid amplification monitor of any one of embodiments 48-50, wherein the polymer is a solid at an ambient temperature and a liquid at an amplification temperature.

Embodiment 52

The nucleic acid amplification monitor of any one of embodiments 28-51, wherein the sample chamber, reaction-diffusion conduit, or both are suitable for reverse transcription.

Embodiment 53

The nucleic acid amplification monitor of any one of embodiments 28-52, wherein the substrate is a polymeric chip.

Embodiment 54

The nucleic acid amplification monitor of embodiment 53, wherein the polymeric chip comprises polymethyl methacrylate (PMMA).

Embodiment 55

A method of quantifying nucleic acid amplification comprising amplifying a sample comprising a nucleic acid molecule in the device of any one of embodiments 1-27, or the nucleic acid amplification monitor of any one of embodiments 28-54 to generate an amplified nucleic acid molecule and measuring a reaction-diffusion length of said amplified nucleic acid molecule through the one or more conduits, wherein reaction-diffusion length is proportional to the number of nucleic acid copies in the sample.

Embodiment 56

The method of embodiment 55, wherein amplifying the nucleic acid molecule comprises thermo-cycling or isothermal nucleic acid amplification.

Embodiment 57

The method of embodiment 55 or 56, further comprising comparing the reaction-diffusion length of the one or more reaction-diffusion conduits.

Embodiment 58

The method of embodiment 55-57, further comprising comparing the reaction-diffusion length of the one or more reaction-diffusion conduits to a control

Embodiment 59

The method of any one of embodiments 55-58, wherein the nucleic acid molecule is RNA.

Embodiment 60

The method of embodiment 59, further comprising, prior to the amplifying, reverse transcribing the RNA to generate cDNA.

Embodiment 61

A method of identifying an unknown nucleic acid molecule, comprising: amplifying a sample comprising an unknown nucleic acid molecule in the device of any one of embodiments 1-27, or the nucleic acid amplification monitor of any one of embodiments 28-54, wherein each of the at least one conduits contain a plurality of primers specific for a different known nucleic acid molecule; and measuring a reaction-diffusion length within the reaction-diffusion conduit, wherein the presence of the reaction-diffusion length indicates that the sample having an unknown nucleic acid molecule comprises the known nucleic acid molecule to which the primers in the at least one conduit are specific and the extent of the reaction-diffusion length within the conduit indicates the number of the unknown nucleic acid molecules in the sample.

Embodiment 62

The method of embodiment 61, comprising determining the difference in length of reaction-diffusion from a nuclemeter having a sample having a known quantity of a nucleic acid and a nuclemeter having a sample having an unknown nucleic acid molecule, wherein the difference in the length of the reaction-diffusion between the known quantity of a nucleic acid molecule and the sample having an unknown nucleic acid molecule indicates a number of nucleic acid molecules in the sample having the unknown nucleic acid molecule.

Embodiment 63

A system for monitoring nucleic acid amplification comprising: a nuclemeter comprising a sample chamber, at least one reaction-diffusion conduit in fluid communication with the sample chamber, each of the sample chamber and the conduit being capable of holding a blend of reactants for nucleic acid amplification; an optical imager; and a heat source.

Embodiment 64

The system of embodiment 63, further comprising a controller.

Embodiment 65

The system of any one of embodiments 63 or 64, further comprising an output device.

Embodiment 66

The system of embodiment 65, each of the optical imager, heat source and output device being operably controlled by the controller.

What is claimed:
1. A device for monitoring nucleic acid amplification, the device comprising:
   at least one nuclemeter, comprising:
   (a) a sample chamber;
   (b) one or more reaction-diffusion conduits, the one or more reaction-diffusion conduits being in fluid communication with the sample chamber;
   wherein the sample chamber, the one or more reaction-diffusion conduits, or the sample chamber and the one or more reaction-diffusion conduits contain a polymer comprising one or more amplification reagents;
   (c) a removable barrier located between the sample chamber and each of the one or more reaction-diffusion conduits, wherein the removable barrier comprises a material that degrades, dissolves, melts, or any combination thereof; and

(d) a measuring device configured to measure a reaction-diffusion length along the one or more reaction-diffusion conduits.

2. The device of claim 1, wherein the polymer comprises a gel, hydroxypropyl-methyl-cellulose (HPMC), or a solid.

3. The device of claim 2, wherein the polymer is a solid at an ambient temperature and a liquid at an amplification temperature.

4. The device of claim 1, comprising about 2 to about 100 reaction-diffusion conduits in fluid communication with the sample chamber.

5. The device of claim 1 comprising a plurality of sample chambers.

6. The device of claim 5, wherein at least some of the sample chambers comprise one or more reaction-diffusion conduits in fluid communication therewith.

7. The device of claim 6, wherein at least one sample chamber has therein a known quantity of a preselected, target nucleic acid molecule.

8. The device of claim 1, wherein the sample chamber has a porous membrane that specifically binds nucleic acids and allows other non-nucleic acid material to pass through.

9. The device of claim 1, further comprising a waste conduit, a light source, an optical imager, a heat source, or any combination thereof, wherein the waste conduit is in fluid communication with the sample chamber and/or the one or more reaction-diffusion conduits.

10. The device of claim 9, wherein the heat source provides a temperature gradient along the one or more reaction-diffusion conduits and/or controls a temperature in the sample chamber and the reaction-diffusion conduit.

11. The device of claim 1, further comprising a blend of reactants in the sample chamber.

12. The device of claim 1, wherein the one or more amplification reagents comprise a plurality of primers, enzymes, or both.

13. The device of claim 12, comprising at least two nuclemeters, each nuclemeter containing different primers.

14. The device of claim 12, wherein at least one of the one or more reaction-diffusion conduits contains a polymer comprising different primers.

15. The device of claim 1, further comprising a substrate, wherein a plurality of nuclemeters are disposed on or form a part of the substrate.

16. The device of claim 15, wherein the substrate is a polymeric chip.

17. The device of claim 16, wherein the polymeric chip comprises polymethyl methacrylate (PMMA).

18. The device of claim 1, wherein the measuring device comprises a ruler positioned along the length of the one or more reaction-diffusion conduits.

19. The device of claim 1, wherein the sample chamber and the one or more reaction-diffusion conduits are configured for detection of amplified nucleic acid molecules in the sample chamber and/or along the length of the one or more reaction-diffusion conduits in real time.

20. The device of claim 1, comprising means for detecting amplified nucleic acid molecules in the sample chamber and along the length of the reaction-diffusion conduit.

* * * * *